United States Patent
Sun et al.

(10) Patent No.: US 7,872,005 B2
(45) Date of Patent: Jan. 18, 2011

(54) 2-SUBSTITUTED HETEROARYL COMPOUNDS

(75) Inventors: Lijun Sun, Harvard, MA (US); Zachary Demko, Somerville, MA (US); Yumiko Wada, Billerica, MA (US); Shijie Zhang, Nashua, NH (US)

(73) Assignee: Synta Pharmaceuticals Corporation, Lexington, MA (US)

( * ) Notice: Subject to any disclaimer, the term of this patent is extended or adjusted under 35 U.S.C. 154(b) by 632 days.

(21) Appl. No.: 11/174,173

(22) Filed: Jul. 1, 2005

(65) Prior Publication Data

US 2006/0063739 A1 Mar. 23, 2006

Related U.S. Application Data

(60) Provisional application No. 60/585,124, filed on Jul. 1, 2004.

(51) Int. Cl.
*C07D 413/04* (2006.01)
*A61K 31/535* (2006.01)

(52) U.S. Cl. .................... 514/235.8; 544/122
(58) Field of Classification Search .......... 544/122; 514/235.8
See application file for complete search history.

(56) References Cited

U.S. PATENT DOCUMENTS

| 6,660,733 | B2 | 12/2003 | Sun et al. |
| 6,680,315 | B2 | 1/2004 | Ono et al. |
| 6,693,097 | B2 | 2/2004 | Ono et al. |
| 6,858,606 | B2 | 2/2005 | Sun et al. |
| 6,958,332 | B2 | 10/2005 | Sun et al. |
| 7,045,517 | B2 | 5/2006 | Ono et al. |
| 7,067,514 | B2 | 6/2006 | Ono et al. |
| 2005/0250774 | A1 | 11/2005 | Ono et al. |
| 2005/0250787 | A1 | 11/2005 | Sun et al. |
| 2005/0282809 | A1 | 12/2005 | Ono et al. |
| 2006/0025409 | A1 | 2/2006 | Ono et al. |
| 2006/0030560 | A1 | 2/2006 | Sun et al. |
| 2006/0063739 | A1 | 3/2006 | Sun et al. |
| 2006/0069090 | A1 | 3/2006 | Ono et al. |
| 2006/0122156 | A1 | 6/2006 | Sun et al. |
| 2006/0135518 | A1 | 6/2006 | Wada et al. |

FOREIGN PATENT DOCUMENTS

WO WO 03/010239 A1 * 2/2003
WO WO 03/047516 A2 * 6/2003

OTHER PUBLICATIONS

Concise Encyclopedia Chemistry (1993) Walter de Gruyter Berlin-New York.*
A Maureen Rouhi, Chemical & Engineering News, Feb. 24, 2003, pp. 32-35.*
Byrn et al., Solid-State Chemistry of Drugs, Second Edition, 1999, pp. 233-247.*
U.S. Appl. No. 10/561,025, Nagai et al.

* cited by examiner

*Primary Examiner*—Rebecca L Anderson
(74) *Attorney, Agent, or Firm*—Edwards Angell Palmer & Dodge LLP; Jeffrey D. Hsi; Mark D. Russett

(57) ABSTRACT

This invention relates to compounds of formula (I):

$$R_3-G-(C)_m-Y \underset{U}{\overset{N}{\underset{\parallel}{\bigcirc}}} X-R_1$$
$$\underset{R_4}{\overset{R_2}{}} \quad R_6$$

(I)

or pharmaceutically acceptable salts, solvate, clathrates hydrates or polymorphs thereof, their compositions and methods of use and methods of making thereof. The compounds (and compositions) are useful in modulating IL-12 production and processes mediated by IL-12.

34 Claims, No Drawings

2-SUBSTITUTED HETEROARYL COMPOUNDS

CROSS REFERENCE TO RELATED APPLICATIONS

This application claims the benefit of U.S. provisional patent application Ser. No. 60/585,124, filed on Jul. 1, 2004, the contents of which are hereby incorporated herein by reference in their entirety.

BACKGROUND

Interleukin-12 (IL-12) is a heterodimeric cytokine (p70) composed of two subunits (p35 and p40), and plays key roles in immune responses by bridging innate resistance and antigen-specific adaptive immunity. Trinchieri (1993) *Immunol Today* 14: 335. For example, it promotes type 1 T helper cell (Th1) responses and, hence, cell-mediated immunity. Chan et al. (1991) *J Exp Med* 173: 869; Seder et al. (1993) *Proc Natl Acad Sci USA* 90: 10188; Manetti et al. (1993) *J Exp Med* 177: 1199; and Hsieh et al. (1993) *Science* 260: 547. Overproduction of IL-12 causes excessive Th1 responses, and may result in inflammatory disorders, such as insulin-dependent diabetes mellitus, multiple sclerosis, rheumatoid arthritis, psoriasis, Crohn's disease, or sepsis. See, for example, Gately et al. (1998) *Annu Rev Immunol.* 16: 495; and Abbas et al. (1996) *Nature* 383: 787. Thus, inhibiting IL-12 overproduction is an approach to treating the just-mentioned diseases. Trembleau et al. (1995) *Immunol. Today* 16: 383; and Adorini et al. (1997) *Chem. Immunol.* 68: 175. For example, overproduction of IL-12 and the resultant excessive Th1 type responses can be suppressed by modulating IL-12 production. Therefore, compounds that down-regulates IL-12 production can be used for treating inflammatory diseases. Ma et al. (1998) *Eur Cytokine Netw* 9: 54.

SUMMARY

The invention relates to heterocyclic compounds, compositions including the compounds and methods of using and methods of making thereof. The compounds (and compositions) are useful in modulating IL-12 production and processes mediated by IL-12.

One aspect is a compound of formula (I) or pharmaceutically acceptable salt, solvate, clathrate, hydrate or polymorph thereof:

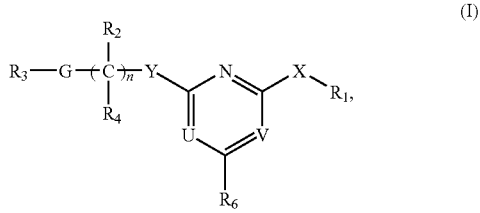

(I)

wherein
$R_1$ is

—$N(R^c)(CH_2)_nR^c$; cycloalkyl, aryl, or heteroaryl;
for each occurrence, each of $R_2$ and $R_4$, independently, is $R^c$, halogen, nitro, cyano, isothionitro, $SR^c$, or $OR^c$; or $R_2$ and $R_4$, taken together, is carbonyl.

$R_3$ is $R^c$, alkenyl, alkynyl, $OR^c$, $OC(O)R^c$, $SO_2R^c$, $S(O)R^c$, $S(O_2)NR^cR^d$, $SR^c$, $NR^cR_d$, $NR^cCOR^d$, $NR^cC(O)OR^d$, $NR^cC(O)NR^cR^d$, $NR^cSO_2R^d$, $C(O)R^c$, $C(O)R^c$, $C(O)OR^c$, or $C(O)NR^cR^d$; $P(O)OR^cOR^d$; $S(O)_2NR^cR^d$;
$R_5$ is H or alkyl;
$R_6$ is

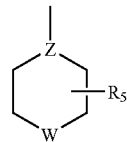

Each n is independently 0, 1, 2, 3, 4, 5, or 6;
G is:
Hydrazide (such as, for example, —C(O)NHNH—, —NHNHC(O)—, —C(O)NR$^f$NR$^g$—, or —NR$^f$NR$^g$C(O)—;
Hydrazone (such as, for example, —CH=N—NH—, —NH—N=CH—, —CR$^g$=N—NR$^f$—, or —NR$^f$—N=CR$^g$—);
Hydrazine (such as, for example, —NHNH— or —NR$^f$NR$^g$—);—
Hydroxylamine (such as, for example, —NHO—, —O—NH—, —NR$^c$O—, or —O—NR$^c$—);
Oxime (such as, for example, CH=N—O—, —O—N=CH—, —CR$^f$=N—O—, or —O—N=CR$^f$—);
Carbamate (such as, for example, —O—C(O)—NH— and —O—C(O)—NR$^f$—);
Thiocarbanate (such as, for example, —O—C(S)—NH—, —NH—C(S)—O—, —O—C(S)—NR$^f$—, and —NR$^f$—C(S)—O—);
Guanidine (such as, for example, —NH—C(NH)—NH— and —NR$^f$—C(NR$^g$)—NR$^h$—);
Alkylguanidine (such as, for example, —NR$^c$—C(NH)—NH—, and —NR$^c$—C(NR$^c$)—NH—);
Cyanoguanidine (such as, for example, —NH—C(N(CN))—NH—);
Sulfonylguanidine (such as, for example, —NH—C(NSO$_2$R$^c$)—NH— or —NR$^c$—C(NSO$_2$R$^d$)—NH—);
Nitroguanidine (such as, for example, —NH—C(NNO$_2$)—NH—);
Acylguanidine (such as, for example, —NH—C(NC(O)R$^c$)—NH—);
Urea (such as, for example, —NH—C(O)—NH— or —NR$^c$—C(O)—NR$^c$—);
Thiourea (such as, for example, —NH—C(S)—NH— or —NR$^c$—C(S)—NR$^c$—);
—NH—S(O)$_2$—NH—;
—NR$^c$—S(O)$_2$—NR$^c$—;
Sulfamide (such as, for example, —N(R$^c$)—S(O)$_2$—O—);
Phosphoryl (such as, for example, —P(O)(R$^c$)—, —P(O)(R$^c$)—O—, or —P(O)(R$^c$)—NR$^c$—);
-Cyclyl-;
-Heterocyclyl-;
-Aryl-;
-Heteroaryl-;
-Heteroarylalkyl-;
-Heteroaryl-NR$^c$ (such as, for example, -Heteroaryl-NH—);
-Heteroaryl-S—;
-Heteroarylalkyl-O—;
—C(N—CN)—NR$^c$—;
—Si(OH)$_2$—;

—B(OH)—
—C(NR$_d$)—NR$^c$— (such as, for example, C(NH)—NH—);
—N(R$^c$)—CHR$^d$—C(O)—;
—C(O)—ON(R$^c$)—;
—C(O)—N(R$^c$)O—;
—C(S)—ON(R$^c$)—;
—C(S)—N(R$^c$)O—;
—C(N(R$^d$))—ON(R$^c$)—;
—C(N(R$^d$))—NR$^c$O—;
—OS(O)$_2$—N(R$^c$)N(R$^c$)—;
—OC(O)—N(R$^c$)N(R$^c$)—;
—OC(S)—N(R$^c$)N(R$^c$)—;
—OC(N(R$^d$))—N(R$^c$)N(R$^c$)—;
—N(R$^c$)N(R$^c$)S(O)$_2$O—;
—N(R$^c$)N(R$^c$)C(S)O—;
—N(R$^c$)N(R$^c$)C(N(R$^d$))O—;
—OP(O)$_2$O—;
—N(R$^c$)P(O)$_2$O—;
—OP(O)$_2$N(R$^c$)—;
—N(R$^c$)P(O)$_2$N(R$^c$)—;
—P(O)$_2$O—;
—P(O)$_2$N(R$^c$)—;
—N(R$^c$)P(O)$_2$—;
—OP(O)$_2$—;
—O-alkyl-heterocyclyl-N(R$^c$)—;
—N(R$^c$)CHR$^d$C(O)N(R$^c$)CHR$^d$C(O)—;
—N(R$^c$)CHR$^d$C(O)—;
—N(R$^c$)C(O)CHR$^d$—;
—C(O)N(R$^c$)CHR$^d$C(O)—;

X is O, S, S(O), S(O$_2$), N(SO$_2$R$^c$), or NR$^c$;

Y is a covalent bond, CH$_2$, C(O), C=N—R$^c$, C=N—OR$^c$, C=N—SR$^c$, O, S, S(O), S(O$_2$), or NR$^c$;

Z is N or CH;

U and V are each independently N or CR$^c$; and

W is O, S, S(O), S(O$_2$), NR$^c$, or NC(O)R$^c$;

wherein each of R$^a$ and R$^b$, independently, is H, alkyl, aryl, heteroaryl; and each of R$^c$ and R$^d$, independently, is H, alkyl, aryl, heteroaryl, cyclyl, heterocyclyl, —S(O)$_2$R$^e$, or alkylcarbonyl, each R$^e$ is independently alkyl, aryl, heteroaryl, heterocyclyl or cyclyl, and R$^f$, R$^g$ and R$^h$, for each occurrence is H, alkyl, aryl, heteroaryl, aralkyl, cycle, and heterocyclyl.

In another aspect, this invention features a pharmaceutical composition that includes a pharmaceutically acceptable carrier and at least one of the heterocyclic compounds of this invention (e.g., a compound of formula (I) herein; any compound delineated herein).

In further another aspect, the present invention features a method for treating an IL-12 overproduction-related disorder (e.g., rheumatoid arthritis, sepsis, Crohn's disease, multiple sclerosis, psoriasis, or insulin-dependent diabetes mellitus). The method includes administering to a subject (e.g., a human or an animal) in need thereof an effective amount of one or more heterocyclic compounds of this invention. The method can also include the step of identifying a subject in need of treatment of diseases or disorders described above. The identification can be in the judgment of a subject or a health professional and can be subjective (e.g., opinion) or objective (e.g., measurable by a test or a diagnostic method).

Also within the scope of this invention are compositions containing one or more of the heterocyclic compounds described above for use in treating an IL-12 overproduction-related disorder, and the use of such a composition for the manufacture of a medicament for the just-described use.

Other features, objects, and advantages of the invention will be apparent from the description and from the claims.

DETAILED DESCRIPTION

In one embodiment, the compounds are those of any of the formulae herein wherein one of U and V is N, and the other is CR$^c$. In another embodiment, the compounds are those of any of the formulae herein wherein both U and V are N. In another embodiment, the compounds are those of any of the formulae herein wherein both U and V are CR$^c$. In another embodiment, the compounds are those of any of the formulae herein wherein at least one of U and V is independently CR$^c$.

In one embodiment of a compound of the invention, G is —C(O)NHNH—, —NHNHC(O)—, —CH=N—NH—, —NH—N=CH—, —NHNH—, —NHO—, —O—NH—, —NR$^c$—O—, —CH=N—O—, —O—N=CH—, —O—C(S)—NH—, or —NH—C(S)—O—. In another embodiment of a compound of the invention, G is —O—C(O)—NH—, —NH—C(NH)—NH—, —NR$^c$—C(NH)—NH—, —NR$^c$—C(NR$^c$)—NH—, —NH—C(N(CN))—NH—, —NH—C(NSO$_2$R$^c$)—NH—, —NR$^c$—C(NSO$_2$R$^d$)—NH—; —NH—C(NNO$_2$)—NH—, —NH—C(NC(O)R$^c$)—NH—, —NH—C(O)—NH—, or —NH—C(S)—NH—. In another embodiment of a compound of the invention, G is —C(N—CN)—NH—; —Si(OH)$_2$—; —B(OH)—; —C(NH)—NR$^c$—; —N(R$^c$)—CH$_2$—C(O)—; —C(O)—ON(R$^c$)—; —C(O)—N(R$^c$)O—; —C(S)—ON(R$^c$)—; —C(S)—N(R$^c$)O—; —C(N(R$^d$))—ON(R$^c$)—; —C(N(R$^d$))—NR$^c$O—; —OS(O)$_2$—N(R$^c$)N(R$^c$)—; —OC(O)—N(R$^c$)N(R$^c$)—; —OC(S)—N(R$^c$)N(R$^c$)—; —OC(N(R$^d$))—N(R$^c$)N(R$^c$)—; —N(R$^c$)N(R$^c$)S(O)$_2$O—; —N(R$^c$)N(R$^c$)C(S)O—; —N(R$^c$)N(R$^c$)C(N(R$^d$))O—; —OP(O)$_2$O—; —N(R$^c$)P(O)$_2$O—; —OP(O)$_2$N(R$^c$)—; —N(R$^c$)P(O)$_2$N(R$^c$)—; —P(O)$_2$O—; —P(O)$_2$N(R$^c$)—; —N(R$^c$)P(O)$_2$—; —OP(O)$_2$—; —O-alkyl-heterocyclyl-N(R$^c$)—; —N(R$^c$)CHR$^d$C(O)N(R$^c$)CHR$^d$C(O)—; —N(R$^c$)CHR$^d$C(O)—; —N(R$^c$)C(O)CHR$^d$—; or —C(O)N(R$^c$)CHR$^d$C(O)—. In another embodiment of a compound of the invention, G is —NH—S(O)$_2$—NH—, —N(R$^c$)—S(O)$_2$—O—, —P(O)(R$^c$)—, —P(O)(R$^c$)—O—, or —P(O)(R$^c$)—NR$^c$—. In another embodiment of a compound of the invention, G is cyclyl or heterocyclyl. In another embodiment of a compound of the invention, G is cyclopropyl, cyclobutyl, cyclopentyl, cyclohexyl, cycloheptyl, aziridinyl, oxiranyl, azetidinyl, oxetanyl, morpholinyl, or piperidinyl. In another embodiment of a compound of the invention, G is aryl, heteroaryl, heteroarylalkyl, —C(N—CN)—NH—, —Si(OH)$_2$—, —C(NH)—NR$^c$—, or —N(R$^c$)—CH$_2$—C(O)—. In another embodiment of a compound of the invention, G is aryl, heteroaryl, or heteroarylalkyl. In another embodiment of a compound of the invention, G is imidazolyl, imidazolidinone, imidazolidineamine, pyrrolidinyl, pyrrolyl, furanyl, thiophenyl, thiazolyl, triazolyl, oxadiazolyl, thiadiazolyl, pyrazolyl, tetrazolyl, oxazolyl, isoxazolyl, phenyl, pyridyl, pyrimidyl, indolyl, benzothiazolyl, or piperazinyl. In another embodiment of the invention, G is -Heteroaryl-NH—, -Heteroaryl-S—, -Heteroarylalkyl-O—, —C(N—CN)—NH—, —Si(OH)$_2$—, or —C(NH)—NR$^c$—, —N(R$^c$)—CH$_2$—C(O)—.

In one embodiment of a compound of the invention, X is NR$^c$. In another embodiment of a compound of the invention, X is NR$^c$, and R$^c$ in X is H, alkyl, or alkylcarbonyl. In another embodiment of a compound of the invention, X is O.

In one embodiment of a compound of the invention, $R_1$ is $$N=\begin{array}{c}R^a\\\diagup\\\diagdown\\R^b\end{array}$$

In another embodiment of a compound of the invention, $R_1$ is $$N=\begin{array}{c}R^a\\\diagup\\\diagdown\\R^b\end{array},$$

and one of $R^a$ or $R^b$ is H. In another embodiment of the compound of the invention, $R_1$ is $$N=\begin{array}{c}R^a\\\diagup\\\diagdown\\R^b\end{array},$$

and one of $R^a$ or $R^b$ is alkyl. In another embodiment of the compound of the invention, $R_1$ is $$N=\begin{array}{c}R^a\\\diagup\\\diagdown\\R^b\end{array},$$

and one of $R^a$ or $R^b$ is aryl. In another embodiment of the compound of the invention, $R_1$ is $$N=\begin{array}{c}R^a\\\diagup\\\diagdown\\R^b\end{array},$$

and one of $R^a$ or $R^b$ is heteroaryl.

In another embodiment of the compound of the invention, $R_1$ is aryl or heteroaryl.

In one embodiment of a compound of the invention, U is N and V is $CR^c$. In another embodiment of the compound of the invention, U is N and V is $CR^c$, and $R^c$ in V is H. In another embodiment of the compound of the invention, U is CRC and V is N. In another embodiment of the compound of the invention, U is CRC and V is N, and $R^c$ in U is H.

In one embodiment of a compound of the invention, Z is N.

In one embodiment of a compound of the invention, W is O.

In one embodiment of a compound of the invention, $R_5$ is H.

In one embodiment of a compound of the invention, Y is $CH_2$, O, or a covalent bond.

In one embodiment of a compound of the invention, n is 0, 1, or 2.

In one embodiment, the compound of a formula herein is that wherein $R_6$ is morpholinyl.

In one embodiment of a compound of the invention, each of $R_2$ and $R_4$ is $R^c$. In another embodiment of a compound of the invention, each of $R_2$ and $R_4$ is $R^c$, and $R^c$ is H. In another embodiment of a compound of the invention, each of $R_2$ and $R_4$ is $R^c$, and each $R^c$ is independently alkyl. In another embodiment of a compound of the invention, each of $R_2$ and $R_4$ is $R^c$, and $R^c$ in $R_4$ is alkyl. In another embodiment of a compound of the invention, each of $R_2$ and $R_4$ is $R^c$, and $R^c$ in $R_4$ is H.

In one embodiment of a compound of the invention, $R_3$ is $R^c$, $COR^c$, $C(O)R^c$, $SO_2R^c$, or $S(O)_2NR^cR^d$. In another embodiment of a compound of the invention, $R_3$ is $R^c$, and $R^c$ in $R_3$ is H, alkyl, aryl, cyclyl, or heterocyclyl. In another embodiment of a compound of the invention, $R_3$ is $COR^c$, and $R^c$ in $R_3$ is H. In another embodiment of a compound of the invention, $R_3$ is $SO_2R^c$, and $R^c$ in $R_3$ is cyclyl.

In one embodiment, the invention provides a pharmaceutical composition comprising an effective amount of a compound of formula (I) or a pharmaceutically acceptable salt, solvate, clathrate, hydrate or polymorph thereof:

(I)

$$R_3-G-(C)_n-Y\begin{array}{c}R_2\\|\\R_4\end{array}\diagdown\begin{array}{c}N\\\diagup\quad\diagdown\\U\quad\quad V\\\diagdown\quad\diagup\\R_6\end{array}X\diagdown R_1,$$

wherein
$R_1$ is $$N=\begin{array}{c}R^a\\\diagup\\\diagdown\\R^b\end{array},$$

—$N(R^c)(CH_2)_nR^c$; cycloalkyl, aryl, or heteroaryl;

for each occurrence, each of $R_2$ and $R_4$, independently, is $R^c$, halogen, nitro, cyano, isothionitro, $SR^c$, or $OR^c$; or $R_2$ and $R_4$, taken together, is carbonyl.

$R_3$ is $R^c$, alkenyl, alkynyl, $OR^c$, $OC(O)R^c$, $SO_2R^c$, $S(O)R^c$, $S(O_2)NR^cR^d$, $SR^c$, $NR^cR^d$, $NR^cCOR^d$, $NR^cC(O)OR^d$, $NR^cC(O)NR^cR^d$, $NR^cSO_2R^d$, $C(O)R^c$, $C(O)R^c$, $C(O)OR^c$, or $C(O)NR^cR^d$; $P(O)OR^cOR^d$; $S(O)_2NR^cR^d$;

$R_5$ is H or alkyl;
$R_6$ is $$\begin{array}{c}Z\\|\\\diagup\quad\diagdown\\|\quad\quad|-R_5\\\diagdown\quad\diagup\\W\end{array}$$

Each n is independently 0, 1, 2, 3, 4, 5, or 6;
G is:
Hydrazide (such as, for example, —C(O)NHNH—, —NHNHC(O)—, —C(O)NR$^f$NR$^g$—, or —NR$^f$NR$^g$C(O)—;
Hydrazone (, such as, for example, —CH=N—NH—, —NH—N=CH—, —CR$^g$=N—NR$^f$—, or —NR$^f$—N=CR$^g$—);—

Hydrazine (such as, for example, —NHNH— or —NR$^f$NR$^g$—);—
Hydroxylamine (such as, for example, —NHO—, —O—NH—, —NR$^c$O—, or —O—NR$^c$—);—
Oxime (such as, for example, CH=N—O—, —O—N=CH—, —CR$^f$=N—O—, or —O—N=CR$^f$—);—
Carbamate (such as, for example, —O—C(O)—NH— and —O—C(O)—NR$^f$—);—
Thiocarbamate (such as, for example, —O—C(S)—NH—, —NH—C(S)—O—, —O—C(S)—NR$^f$—, and —NR$^f$—C(S)—O—);—
Guanidine (such as, for example, —NH—C(NH)—NH— and —NR$^f$—C(NR$^g$)—NR$^h$—);—
Alkylguanidine (such as, for example, —NR$^c$—C(NH)—NH—, and —NR$^c$—C(NR$^c$)—NH—);
Cyanoguanidine (such as, for example, —NH—C(N(CN))—NH—);
Sulfonylguanidine (such as, for example, —NH—C(NSO$_2$R$^c$)—NH— or —NR$^c$—C(NSO$_2$R$^d$)—NH—);—
Nitroguanidine (such as, for example, —NH—C(NNO$_2$)—NH—);
Acylguanidine (such as, for example, —NH—C(NC(O)R$^c$)—NH—);
Urea (such as, for example, —NH—C(O)—NH— or —NR$^c$—C(O)—NR$^c$—);
Thiourea (such as, for example, —NH—C(S)—NH— or —NR$^c$—C(S)—NR$^c$—);
—NH—S(O)$_2$—NH—;
—NR$^c$—S(O)$_2$—NR$^c$—;
Sulfamide (such as, for example, —N(R$^c$)—S(O)$_2$—O—);
Phosphoryl (such as, for example, —P(O)(R$^c$)—, —P(O)(R$^c$)—O—, or —P(O)(R$^c$)—NR$^c$—);
-Cyclyl-;
-Heterocyclyl-;
-Aryl-;
-Heteroaryl-;
-Heteroarylalkyl-;
-Heteroaryl-NR$^c$ (such as, for example, -Heteroaryl-NH—);
-Heteroaryl-S—;
-Heteroarylalkyl-O—;
—C(N—CN)—NR$^c$—;
—Si(OH)$_2$—;
—B(OH)—
—C(NR$^d$)—NR$^c$— (such as, for example, C(NH)—NH—);
—N(R$^c$)—CHR$^d$—C(O)—;
—C(O)—ON(R$^c$)—;
—C(O)—N(R$^c$)O—;
—C(S)—ON(R$^c$)—;
—C(S)—N(R$^c$)O—;
—C(N(R$^d$))—ON(R$^c$)—;
—C(N(R$^d$))—NR$^c$O—;
—OS(O)$_2$—N(R$^c$)N(R$^c$)—;
—OC(O)—N(R$^c$)N(R$^c$)—;
—OC(S)—N(R$^c$)N(R$^c$)—;
—OC(N(R$^d$))—N(R$^c$)N(R$^c$)—;
—N(R$^c$)N(R$^c$)S(O)$_2$O—;
—N(R$^c$)N(R$^c$)C(S)O—;
—N(R$^c$)N(R$^c$)C(N(R$^d$))O—;
—OP(O)$_2$O—;
—N(R$^c$)P(O)$_2$O—;
—OP(O)$_2$N(R$^c$)—;
—N(R$^c$)P(O)$_2$N(R$^c$)—;
—P(O)$_2$O—;
—P(O)$_2$N(R$^c$)—;
—N(R$^c$)P(O)$_2$—;
—OP(O)$_2$—;
—O-alkyl-heterocyclyl-N(R$^c$)—;
—N(R$^c$)CHR$^d$C(O)N(R$^c$)CHR$^d$C(O)—;
—N(R$^c$)CHR$^d$C(O)—;
—N(R$^c$)C(O)CHR$^d$—;
—C(O)N(R$^c$)CHR$^d$C(O)—;
X is O, S, S(O), S(O$_2$), N(SO$_2$R$^c$), or NR$^c$;
Y is a covalent bond, CH$_2$, C(O), C=N—R$^c$, C=N—OR$^c$, C=N—SR$^c$, O, S, S(O), S(O$_2$), or NR$^c$;
Z is N or CH;
U and V are each independently N or CR$^c$; and
W is O, S, S(O), S(O$_2$), NR$^c$, or NC(O)R$^c$;

wherein each of R$^a$ and R$^b$, independently, is H, alkyl, aryl, heteroaryl; and each of R$^c$, and R$^d$, independently, is H, alkyl, aryl, heteroaryl, cyclyl, heterocyclyl, —S(O)$_2$R$^e$, or alkylcarbonyl, each R$^e$ is independently alkyl, aryl, heteroaryl, heterocyclyl or cyclyl, and R$^f$, R$^g$ and R$^h$, for each occurrence is H, alkyl, aryl, heteroaryl, aralkyl, cycle, and heterocyclyl, and a pharmaceutically acceptable carrier.

In another embodiment, the invention provides a method of treating an IL-12 overproduction-related disorder, comprising administering to a subject in need thereof a therapeutically effective amount of a compound of formula (I) or a pharmaceutically acceptable salt thereof.

The method includes administering to the subject (including a subject identified as in need of such treatment) an effective amount of a compound described herein, or a composition described herein to produce such effect. Identifying a subject in need of such treatment can be in the judgment of a subject or a health care professional and can be subjective (e.g. opinion) or objective (e.g. measurable by a test or diagnostic method).

In another embodiment of a method of the invention, the disorder is rheumatoid arthritis, sepsis, Crohn's disease, multiple sclerosis, psoriasis, or insulin-dependent diabetes mellitus.

Other embodiments include the compounds, intermediates, or a pharmaceutically acceptable salt, solvate, clathrate, hydrate or polymorph thereof delineated herein, or compositions including them; as well as their methods of use for treatment or prevention of disease, inhibition of IL-12, or modulation of IL-12 mediated disease; and methods of making the compounds and intermediates herein.

Another embodiment is a method of making a compound of any of the formulae herein using any one, or combination of, reactions delineated herein. The method can include the use of one or more intermediates or chemical reagents delineated herein.

Another aspect is a radiolabelled compound of any of the formulae delineated herein. Such compounds have one or more radioactive atoms (e.g., $^3$H, $^2$H, $^{14}$C, $^{13}$C, $^{35}$S, $^{125}$I, $^{131}$I) introduced into the compound. Such compounds are useful for drug metabolism studies and diagnostics.

As used herein, the term "alkyl" refers to a straight-chained or branched hydrocarbon group containing 1 to 12 carbon atoms. The term "lower alkyl" refers to a C1-C6 alkyl chain. Examples of alkyl groups include methyl, ethyl, n-propyl, isopropyl, tert-butyl, and n-pentyl. The term "alkenyl" refers to an unsaturated hydrocarbon chain that may be a straight chain or branched chain, containing 2 to 12 carbon atoms and at least one carbon-carbon double bond. The term "alkynyl" refers to an unsaturated hydrocarbon chain that may be a straight chain or branched chain, containing the 2 to 12 carbon atoms and at least one carbon-carbon triple bond. The sp$^2$ or sp$^3$ carbons may optionally be the point of attachment of the alkenyl or alkynyl groups, respectively.

The term "alkoxy" refers to an —O-alkyl radical. The term "ester" refers to a C(O)O—R$^e$, wherein R$^e$ is an alkyl, aryl, heteroaryl, heterocyclyl, or cyclyl group. An "amido" is an C(O)NH$_2$, and an "N-alkyl-substitited amido" is of the formula C(O)N(H)(R$^e$).

The term "sulfanyl" refers to a thio group.

As used herein, the term "halogen" or "halo" means —F, —Cl, —Br or —I.

Acids and bases useful in the methods herein are known in the art. Acid catalysts are any acidic chemical, which can be inorganic (e.g., hydrochloric, sulfuric, nitric acids, aluminum trichloride) or organic (e.g., camphorsulfonic acid, p-toluenesulfonic acid, acetic acid, ytterbium triflate) in nature. Acids are useful in either catalytic or stoichiometric amounts to facilitate chemical reactions. Bases are any basic chemical, which can be inorganic (e.g., sodium bicarbonate, potassium hydroxide) or organic (e.g., triethylamine, pyridine) in nature. Bases are useful in either catalytic or stoichiometric amounts to facilitate chemical reactions.

Alkylating agents are any reagent that is capable of effecting the alkylation of the functional group at issue (e.g., oxygen atom of an alcohol, nitrogen atom of an amino group). Alkylating agents are known in the art, including in the references cited herein, and include alkyl halides (e.g., methyl iodide, benzyl bromide or chloride), alkyl sulfates (e.g., methyl sulfate), or other alkyl group-leaving group combinations known in the art. Leaving groups are any stable species that can detach from a molecule during a reaction (e.g., elimination reaction, substitution reaction) and are known in the art, including in the references cited herein, and include halides (e.g., I—, Cl—, Br—, F—), hydroxy, alkoxy (e.g., —OMe, —O-t-Bu), acyloxy anions (e.g., —OAc, —OC(O)CF$_3$), sulfonates (e.g., mesyl, tosyl), acetamides (e.g., —NHC(O)Me), carbamates (e.g., N(Me)C(O)O-t-Bu), phosphonates (e.g., —OP(O)(OEt)$_2$), water or alcohols (protic conditions), and the like.

The terms "cycloalkyl" or "cyclyl" refer to a hydrocarbon monocyclic or bicyclic ring system having at least one nonaromatic ring wherein 0, 1, 2, 3, or 4 atoms of each ring may be substituted by a substituent. Examples of cycloalkyl groups include cyclopentyl, cyclohexyl, cyclohexenyl, bicyclo[2.2.1]hept-2-enyl, dihydronaphthalenyl, benzocyclopentyl, and the like.

The term "aryl" refers to a hydrocarbon monocyclic, bicyclic or tricyclic aromatic ring system wherein 0, 1, 2, 3, or 4 atoms of each ring may be substituted by a substituent. Examples of aryl groups include phenyl, naphthyl and the like. The term "arylalkyl" or the term "aralkyl" refers to alkyl substituted with an aryl. The term "arylalkoxy" refers to an alkoxy substituted with aryl.

The term "heteroaryl" refers to an aromatic 5-8 membered monocyclic, 8-12 membered bicyclic, or 11-14 membered tricyclic ring system having 1-3 ring heteroatoms if monocyclic, 1-6 heteroatoms if bicyclic, or 1-9 heteroatoms if tricyclic, said heteroatoms selected from O, N, or S, and the remainder ring atoms being carbon (with appropriate hydrogen atoms unless otherwise indicated) wherein 0, 1, 2, 3, or 4 atoms of each ring may be substituted by a substituent. Examples of heteroaryl groups include pyridyl, furyl or furanyl, pyrrolyl, oxazolyl, pyrimidinyl, quinazolinyl, imidazolyl, benzimidazolyl, thienyl, indolyl, thiazolyl, and the like. The term "heteroarylalkyl" or the term "heteroaralkyl" refers to an alkyl substituted with a heteroaryl. The term "heteroarylalkoxy" refers to an alkoxy substituted with heteroaryl.

The term "heterocyclyl" or "heterocycloalkyl" refers to a nonaromatic 5-8 membered monocyclic, 8-12 membered bicyclic, or 11-14 membered tricyclic ring system comprising 1-3 heteroatoms if monocyclic, 1-6 heteroatoms if bicyclic, or 1-9 heteroatoms if tricyclic, said heteroatoms selected from O, N, S, B, P or Si, wherein 0, 1, 2, 3, or 4 atoms of each ring may be substituted by a substituent. Examples of heterocyclyl groups include tetrahydrofuryl, piperidinyl, piperazinyl, pyrrolidinyl, morpholinyl, thiomorpholinyl, dihydrothiophenyl, 1,4-oxazepanyl, 1H-pyridin-2-onyl and the like. The term "heterocycloalkylalkyl" or the term "heterocyclylalkyl" refers to an alkyl substituted with a heterocyclyl. The term "heterocyclylalkoxy" refers to an alkoxy substituted with heterocyclyl.

Any group that can be substituted (such as, for example, alkyl, alkenyl, alkynyl, aryl, heteroaryl, cyclyl, and heterocyclyl) can be substituted or unsubstituted moieties. The term "substituted" refers to one or more substituents (which may be the same or different), each replacing a hydrogen atom. Examples of substituents include, but are not limited to, halogen (F, Cl, Br, or I), hydroxyl, amino, alkylamino, arylamino, dialkylamino, diarylamino, cyano, nitro, mercapto, oxo (i.e., carbonyl), thio, imino, formyl, carbamido, carbamyl, carboxyl, thioureido, thiocyanato, sulfoamido, sulfonylalkyl, sulfonylaryl, alkyl, alkenyl, alkoxy, thioalkoxy, aryl, heteroaryl, cyclyl, heterocyclyl, wherein alkyl, alkenyl, alkyloxy, aryl, heteroaryl, cyclyl, and heterocyclyl are optionally substituted with alkyl, aryl, heteroaryl, halogen, hydroxyl, amino, mercapto, cyano, nitro, oxo (=O), thioxo (=S), or imino (=NR$^c$).

In other embodiments, substituents on any group (such as, for example, an alkyl, cycloalkyl, aryl, heterocyclyl, or heteroaryl group) can be at any atom of that group. Suitable substituents include, without limitation halogen, CN, NO$_2$, OR$^{15}$, SR$^{15}$, S(O)$_2$OR$^{15}$, NR$^{15}$R$^{16}$, C$_1$-C$_2$ perfluoroalkyl, C$_1$-C$_2$ perfluoroalkoxy, 1,2-methylenedioxy, (=O), (=S), (=NR$^{15}$), C(O)OR$^{15}$, C(O)NR$^{15}$R$^{16}$, OC(O)NR$^{15}$R$^{16}$, NR$^{15}$C(O)NR$^{15}$R$^{16}$, C(NR$^{16}$)NR$^{15}$R$^{16}$, NR$^{15}$C(NR$^{16}$)NR$^5$R$^{16}$, S(O)$_2$NR$^{15}$R$^{16}$, R$^{17}$, C(O)H, C(O)R$^{17}$, NR$_{15}$C(O)R$^{17}$, Si(R$^{15}$)$_3$, OSi(R$^{15}$)$_3$, Si(OH)$_2$R$^{15}$, B(OH)$_2$, P(O)(OR$^{15}$)$_2$, S(O)R$^{17}$, or S(O)$_2$R$^{17}$. Each R$^{15}$ is independently hydrogen, C$_1$-C$_6$ alkyl optionally substituted with cycloalkyl, aryl, heterocyclyl, or heteroaryl. Each R$^{16}$ is independently hydrogen, C$_3$-C$_6$ cycloalkyl, aryl, heterocyclyl, heteroaryl, C$_1$-C$_4$ alkyl or C$_1$-C$_4$ alkyl substituted with C$_3$-C$_6$ cycloalkyl, aryl, heterocyclyl or heteroaryl. Each R$^{17}$ is independently C$_3$-C$_6$ cycloalkyl, aryl, heterocyclyl, heteroaryl, C$_1$-C$_4$ alkyl or C$_1$-C$_4$ alkyl substituted with C$_3$-C$_6$ cycloalkyl, aryl, heterocyclyl or heteroaryl. Each C$_3$-C$_6$ cycloalkyl, aryl, heterocyclyl, heteroaryl and C$_1$-C$_4$ alkyl in each R$^{15}$, R$^{16}$ and R$^{17}$ can optionally be substituted with halogen, CN, C$_1$-C$_4$ alkyl, OH, C$_1$-C$_4$ alkoxy, COOH, C(O)OC$_1$-C$_4$ alkyl, NH$_2$, C$_1$-C$_4$ alkylamino, or C$_1$-C$_4$ dialkylamino.

As used herein, the term "lower" refers to a group having up to six atoms. For example, a "lower alkyl" refers to an alkyl radical having from 1 to 6 carbon atoms, and a "lower alkenyl" or "lower alkynyl" refers to an alkenyl or alkynyl radical having from 2 to 6 carbon atoms, respectively.

Note that unless otherwise depicted, the left atom shown in any substituted group described above is the one closest to the heterocyclic ring. Also note that when n is 2 or greater, the just-described heterocyclic compound may have two or more different C(R$^2$R$^4$) moieties, or when there are more than one group having a designation (e.g., R$^c$-, or R$^d$-containing substituted groups) in a heterocyclic compound, the moieties (e.g., R$^c$, R$^d$) can be the same or different. The same rules apply to other similar situations. Further note that the group (e.g., $R^c$, $R^d$) can in some instances be a monovalent or bivalent substituent.

The compounds of the invention are defined herein by their chemical structures and/or chemical names. Where a compound is referred to by both a chemical structure and a chemical name, and the chemical structure and chemical name conflict, the chemical structure is determinative of the compound's identity.

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., formulation into therapeutic products, intermediates for use in production of therapeutic compounds, isolatable or storable intermediate compounds, treating IL-12 overproduction-related disorders such as rheumatoid arthritis, sepsis, Crohn's disease, multiple sclerosis, psoriasis, or insulin-dependent diabetes mellitus). The compounds produced by the methods herein can be incorporated into compositions, including solutions, capsules, cremes, or ointments for administration to a subject (e.g., human, animal). Such compositions (e.g., pharmaceuticals) are useful for providing to the subject desirable health or other physiological benefits that are associated with such compounds.

Nucleophilic agents are known in the art and are described in the chemical texts and treatises referred to herein. The chemicals used in the aforementioned methods may include, for example, solvents, reagents, catalysts, protecting group and deprotecting group reagents and the like. The methods described above may also additionally include steps, either before or after the steps described specifically herein, to add or remove suitable protecting groups in order to ultimately allow synthesis of the compound of the formulae described herein. The methods delineated herein contemplate converting compounds of one formula to compounds of another formula. The process of converting refers to one or more chemical transformations, which can be performed in situ, or with isolation of intermediate compounds. The transformations can include reacting the starting compounds or intermediates with additional reagents using techniques and protocols known in the art, including those in the references cited herein. Intermediates can be used with or without purification (e.g., filtration, distillation, crystallization, chromatography). Other embodiments relate to the intermediate compounds delineated herein, and their use in the methods (e.g., treatment, synthesis) delineated herein.

Set forth below are exemplary compounds of this invention:

Compound 1

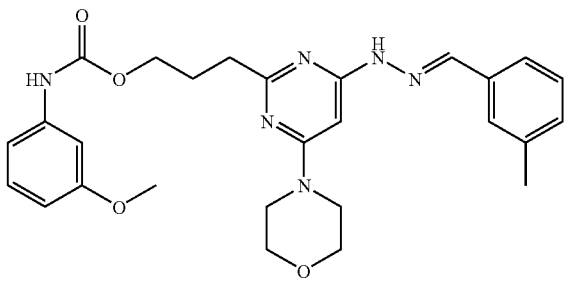

(3-Methoxy-phenyl)-carbamic acid 3-{4-[N'-(3-methyl-benzylidene)-hydrazino]-6-morpholin-4-yl-pyrimidin-2-yl}-propyl ester Compound 2

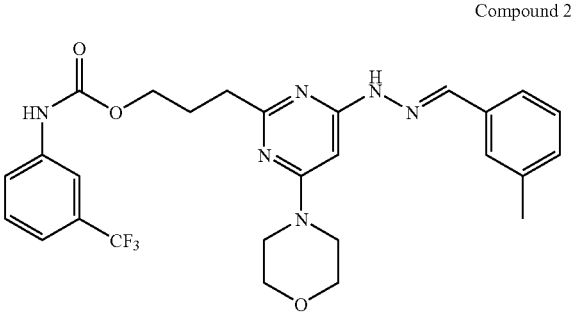

(3-Trifluoromethyl-phenyl)-carbamic acid 3-{4-[N'-(3-methyl-benzylidene)-hydrazino]-6-morpholin-4-yl-pyrimidin-2-yl}-propyl ester Compound 3

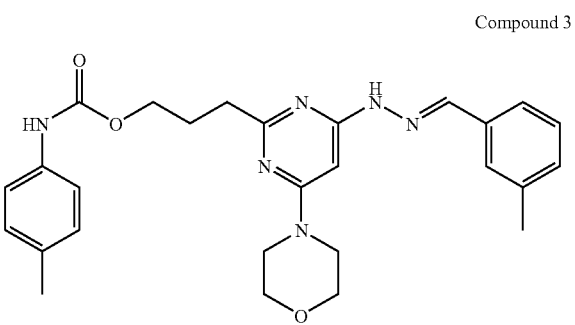

p-Tolyl-carbamic acid 3-{4-[N'-(3-methyl-benzylidene)-hydrazino]-6-morpholin-4-yl-pyrimidin-2-yl}-propyl ester Compound 4

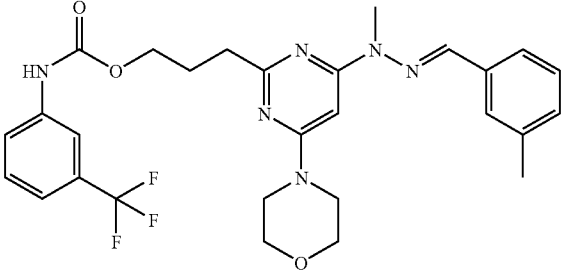

13

(3-Trifluoromethyl-phenyl)-carbamic acid 3-{4-[N-methyl-N'-(3-methyl-benzylidene)-hydrazino]-6-morpholin-4-yl-pyrimidin-2-yl}-propyl ester

14

(4-Nitro-phenyl)-carbamic acid 3-{4-[N'-(3-methyl-benzylidene)-hydrazino]-6-morpholin-4-yl-pyrimidin-2-yl}-propyl ester Compound 5

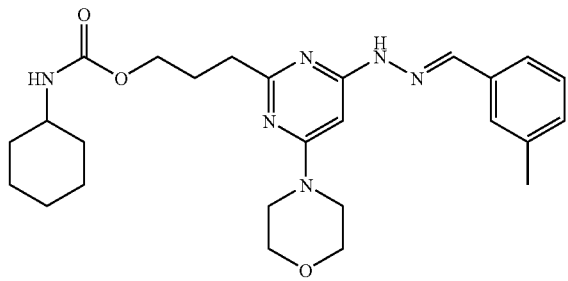

Cyclohexyl-carbamic acid 3-{4-[N'-(3-methyl-benzylidene)-hydrazino]-6-morpholin-4-yl-pyrimidin-2-yl}-propyl ester Compound 8

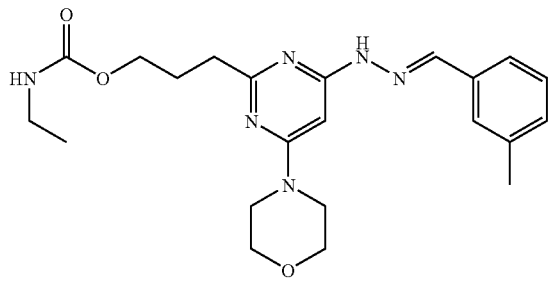

Ethyl-carbamic acid 3-{4-[N'-(3-methyl-benzylidene)-hydrazino]-6-morpholin-4-yl-pyrimidin-2-yl}-propyl ester Compound 6

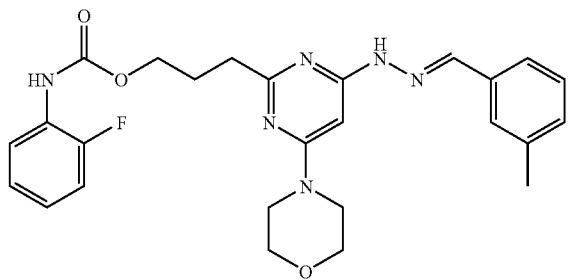

(2-Fluoro-phenyl)-carbamic acid 3-{4-[N'-(3-methyl-benzylidene)-hydrazino]-6-morpholin-4-yl-pyrimidin-2-yl}-propyl ester Compound 9

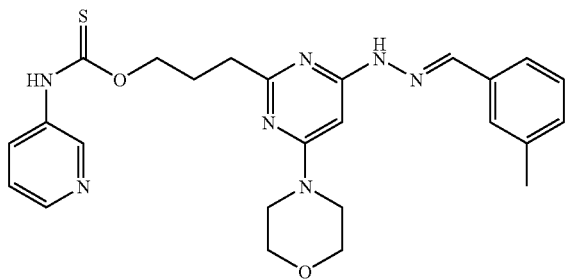

Pyridin-3-yl-thiocarbamic acid O-(3-{4-[N'-(3-methyl-benzylidene)-hydrazino]-6-morpholin-4-yl-pyrimidin-2-yl}-propyl) ester Compound 7

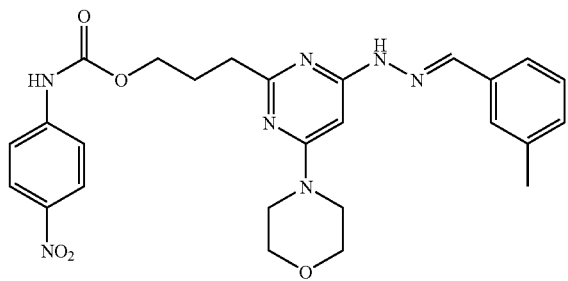

Compound 10

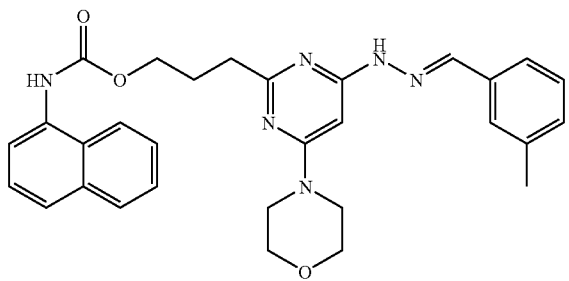

Naphthalen-1-yl-carbamic acid 3-{4-[N'-(3-methyl-benzylidene)-hydrazino]-6-morpholin-4-yl-pyrimidin-2-yl}-propyl ester p-Tolyl-carbamic acid 2-{4-[N'-(3-methyl-benzylidene)-hydrazino]-6-morpholin-4-yl-pyrimidin-2-yl}-ethyl ester Compound 11

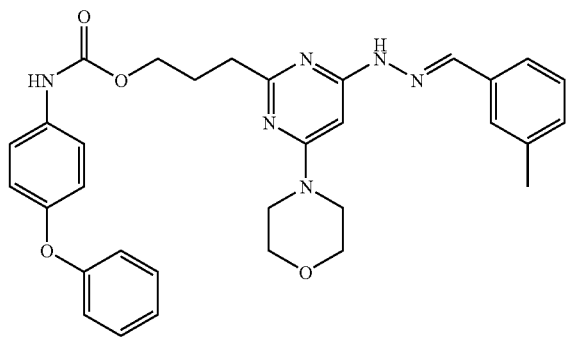

(4-Phenoxy-phenyl)-carbamic acid 3-{4-[N'-(3-methyl-benzylidene)-hydrazino]-6-morpholin-4-yl-pyrimidin-2-yl}-propyl ester Compound 14

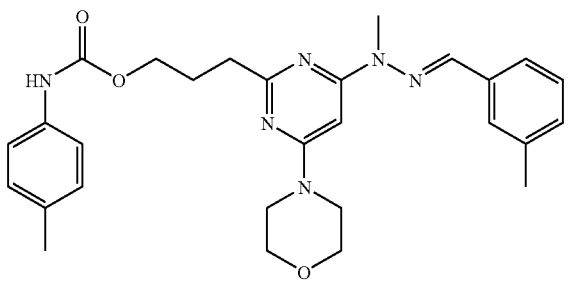

p-Tolyl-carbamic acid 3-{4-[N-methyl-N'-(3-methyl-benzylidene)-hydrazino]-6-morpholin-4-yl-pyrimidin-2-yl}-propyl ester Compound 12

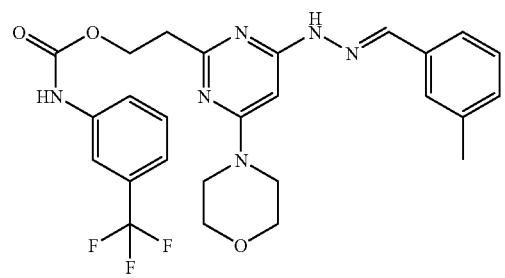

(3-Trifluoromethyl-phenyl)-carbamic acid 2-{4-[N'-(3-methyl-benzylidene)-hydrazino]-6-morpholin-4-yl-pyrimidin-2-yl}-ethyl ester Compound 15

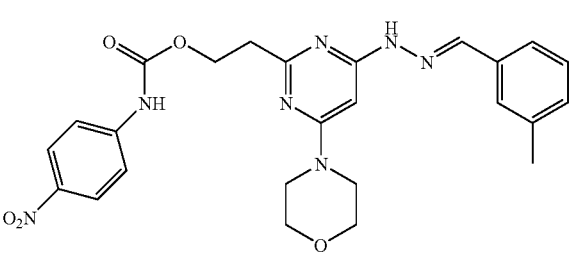

(4-Nitro-phenyl)-carbamic acid 2-{4-[N'-(3-methyl-benzylidene)-hydrazino]-6-morpholin-4-yl-pyrimidin-2-yl}-ethyl ester Compound 13

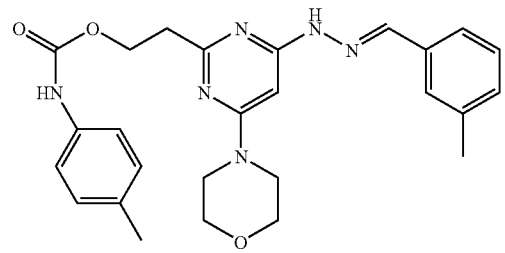

Compound 16

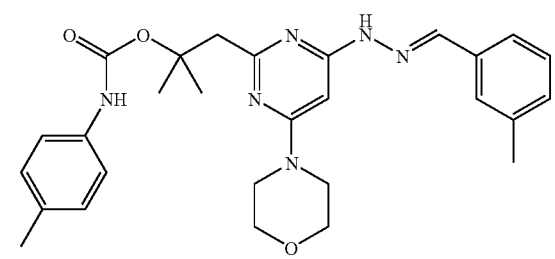

| 17 | 18 |
|---|---|
| p-Tolyl-carbamic acid 1,1-dimethyl-2-{4-[N'-(3-methyl-benzylidene)-hydrazino]-6-morpholin-4-yl-pyrimidin-2-yl}-ethyl ester | p-Tolyl-carbamic acid 2-{4-[N'-(3-methyl-benzylidene)-hydrazino]-6-morpholin-4-yl-pyrimidin-2-yloxy}-ethyl ester |

Compound 17

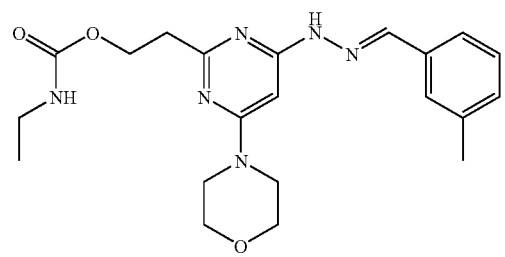

Ethyl-carbamic acid 2-{4-[N'-(3-methyl-benzylidene)-hydrazino]-6-morpholin-4-yl-pyrimidin-2-yl}-ethyl ester Compound 20

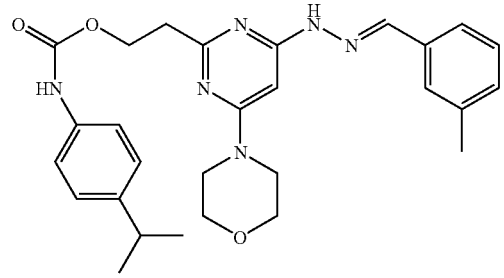

(4-Isopropyl-phenyl)-carbamic acid 2-{4-[N'-(3-methyl-benzylidene)-hydrazino]-6-morpholin-4-yl-pyrimidin-2-yl}-ethyl ester Compound 18

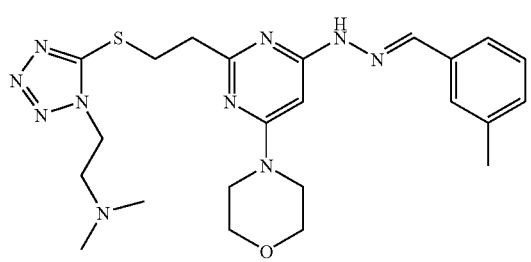

Dimethyl-{2-[5-(2-{4-[N'-(3-methyl-benzylidene)-hydrazino]-6-morpholin-4-yl-pyrimidin-2-yl}-ethyl-sulfanyl)-tetrazol-1-yl]-ethyl}-amine Compound 21

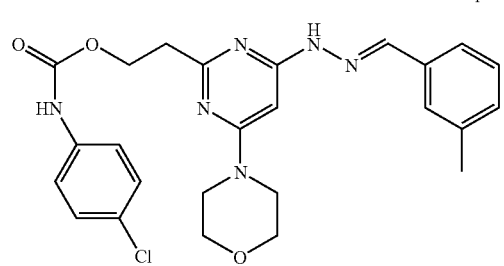

(4-Chloro-phenyl)-carbamic acid 2-{4-[N'-(3-methyl-benzylidene)-hydrazino]-6-morpholin-4-yl-pyrimidin-2-yl}-ethyl ester Compound 19

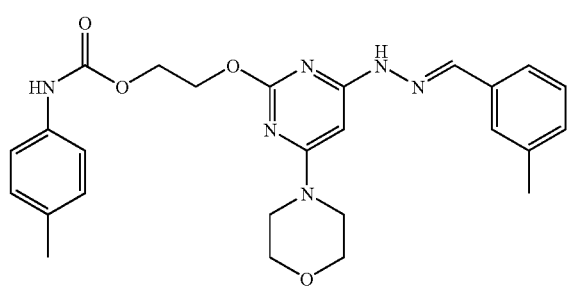

Compound 22

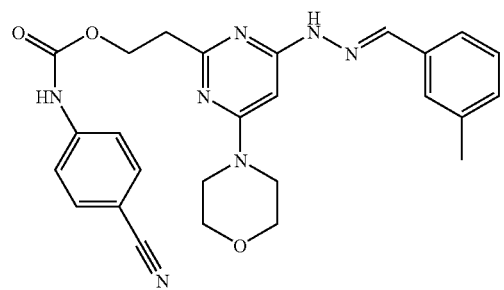

19

(4-Cyano-phenyl)-carbamic acid 2-{4-[N'-(3-methyl-benzylidene)-hydrazino]-6-morpholin-4-yl-pyrimidin-2-yl}-ethyl ester

20

N-(3-Methyl-benzylidene)-N'-{6-morpholin-4-yl-2-[2-(5-pyridin-4-yl-4H-[1,2,4]triazol-3-ylsulfanyl)-ethyl]-pyrimidin-4-yl}-hydrazine Compound 23

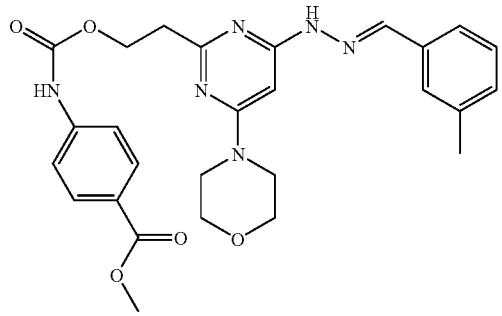

4-(2-{4-[N'-(3-Methyl-benzylidene)-hydrazino]-6-morpholin-4-yl-pyrimidin-2-yl}-ethoxycarbonylamino)-benzoic acid methyl ester Compound 26

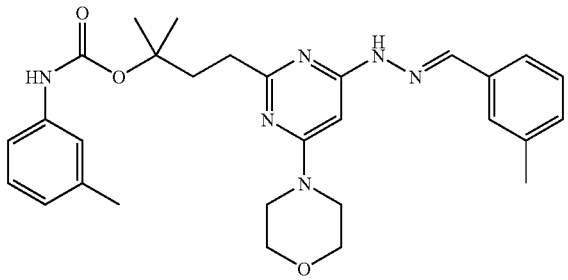

m-Tolyl-carbamic acid 1,1-dimethyl-3-{4-[N'-(3-methyl-benzylidene)-hydrazino]-6-morpholin-4-yl-pyrimidin-2-yl}-propyl ester Compound 24

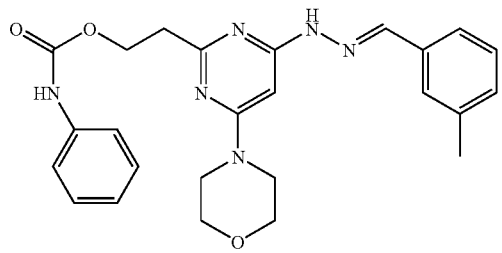

Phenyl-carbamic acid 2-{4-[N'-(3-methyl-benzylidene)-hydrazino]-6-morpholin-4-yl-pyrimidin-2-yl}-ethyl ester Compound 27

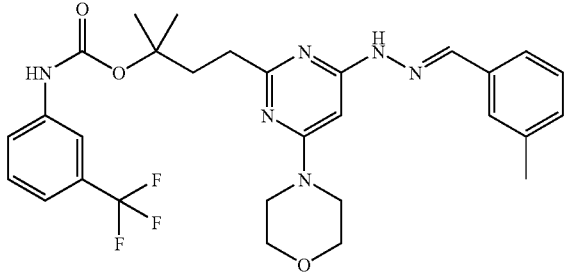

(3-Trifluoromethyl-phenyl)-carbamic acid 1,1-dimethyl-3-{4-[N'-(3-methyl-benzylidene)-hydrazino]-6-morpholin-4-yl-pyrimidin-2-yl}-propyl ester Compound 25

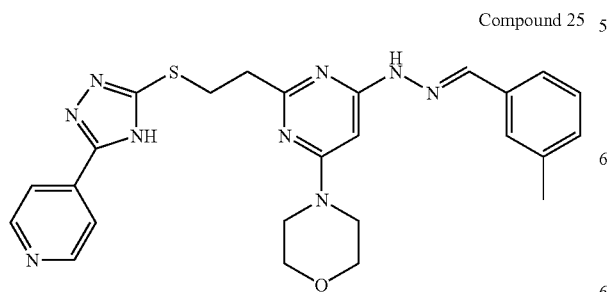

Compound 28

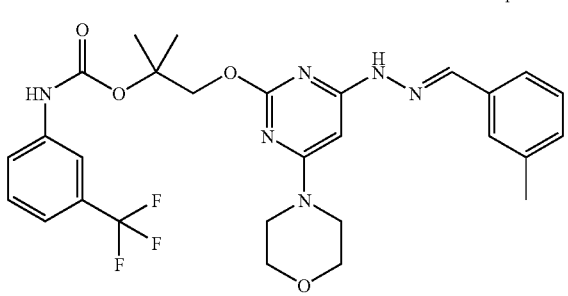

21

(3-Trifluoromethyl-phenyl)-carbamic acid 1,1-dimethyl-2-{4-[N'-(3-methyl-benzylidene)-hydrazino]-6-morpholin-4-yl-pyrimidin-2-yloxy}-ethyl ester

22

N-(2-{4-[N'-(3-Methyl-benzylidene)-hydrazino]-6-morpholin-4-yl-pyrimidin-2-yloxy}-ethyl)-N'-phenyl-cyanoguanidine

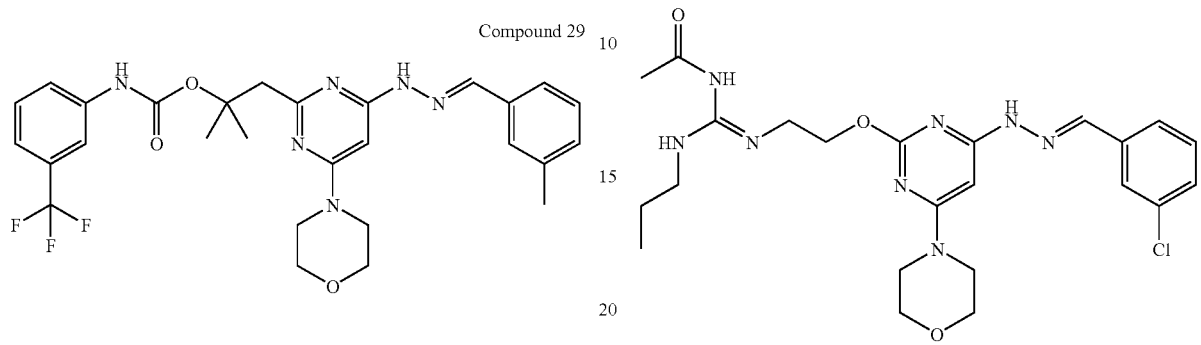

Compound 29

(3-Trifluoromethyl-phenyl)-carbamic acid 1,1-dimethyl-2-{4-[N'-(3-methyl-benzylidene)-hydrazino]-6-morpholin-4-yl-pyrimidin-2-yl}-ethyl ester Compound 32

N-Acetyl-N'-(2-{4-[N'-(3-chloro-benzylidene)-hydrazino]-6-morpholin-4-yl-pyrimidin-2-yloxy}-ethyl)-N''-propyl-guanidine

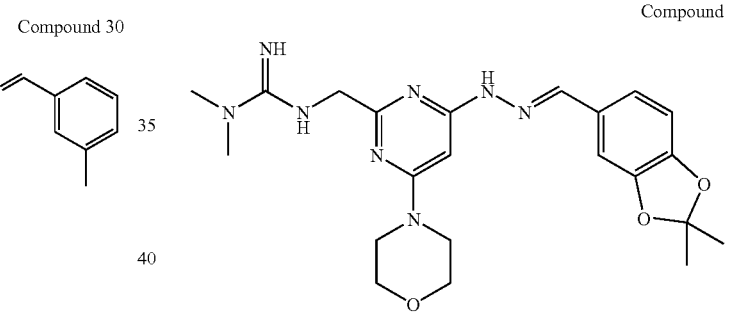

Compound 30

(4-Trifluoromethyl-phenyl)-carbamic acid 1,1-dimethyl-2-{4-[N'-(3-methyl-benzylidene)-hydrazino]-6-morpholin-4-yl-pyrimidin-2-yl}-ethyl ester Compound 33

N'-{4-[N'-(2,2-Dimethyl-benzo[1,3]dioxol-5-ylmethylene)-hydrazino]-6-morpholin-4-yl-pyrimidin-2-ylmethyl}-N,N-dimethyl-guanidine

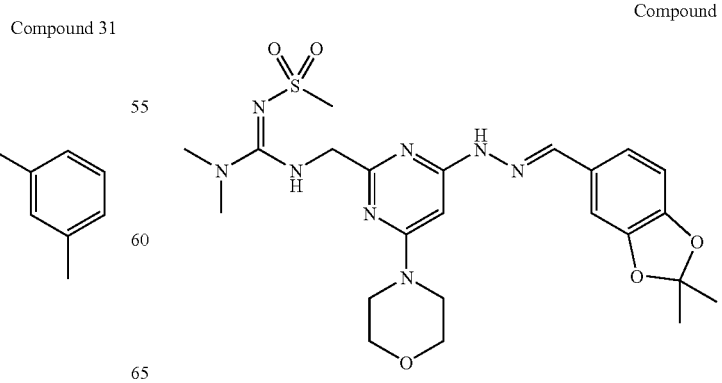

Compound 31

Compound 34

23

N-[Dimethylamino-({4-[N'-(2,2-dimethyl-benzo[1,3]dioxol-5-ylmethylene)-hydrazino]-6-morpholin-4-yl-pyrimidin-2-ylmethyl}-amino)-methylene]-methanesulfonamide

24

N-[4-(N'-Benzofuran-2-ylmethylene-hydrazino)-6-morpholin-4-yl-pyrimidin-2-ylmethyl]-N'-(4-chloro-benzyl)-N''-(4-nitro-benzoyl)-guanidine Compound 35

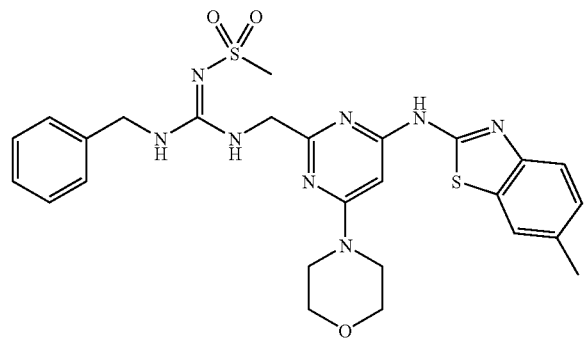

N-(Benzylamino-{[4-(6-methyl-benzothiazol-2-ylamino)-6-morpholin-4-yl-pyrimidin-2-ylmethyl]-amino}-methylene)-methanesulfonamide Compound 38

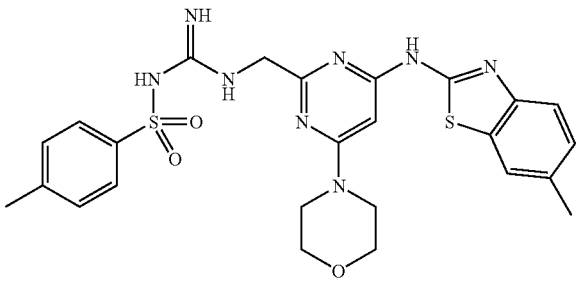

N-[4-(6-Methyl-benzothiazol-2-ylamino)-6-morpholin-4-yl-pyrimidin-2-ylmethyl]-N'-(4-methyl-benzenesolfonyl)-guanidine Compound 36

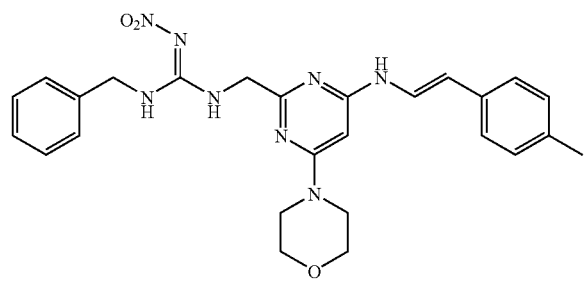

N-Benzyl-N'-[4-morpholin-4-yl-6-(2-p-tolyl-vinylamino)-pyrimidin-2-ylmethyl]-nitroguanidine Compound 39

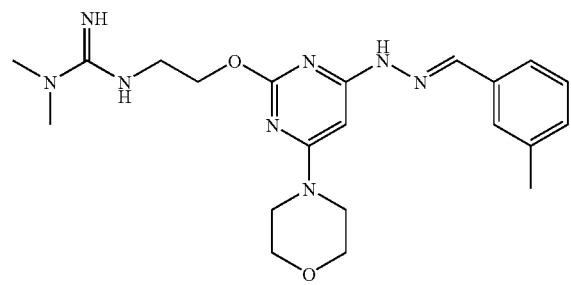

N,N-Dimethyl-N'-(2-{4-[N'-(3-methyl-benzylidene)-hydrazino]-6-morpholin-4-yl-pyrimidin-2-yloxy}-ethyl)-guanidine Compound 37

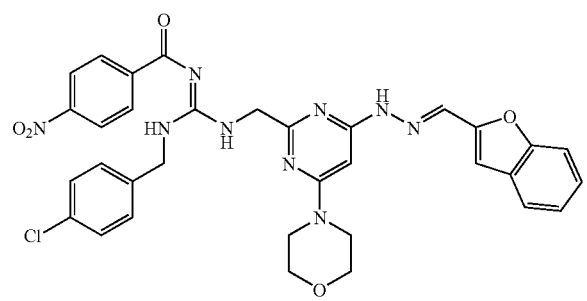

Compound 40

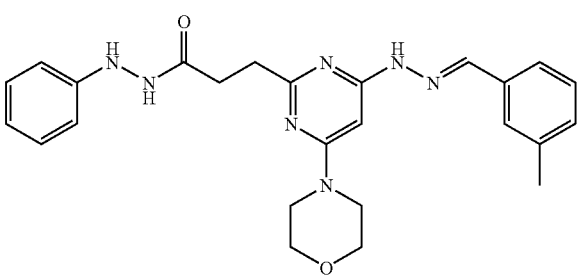

| 25 | 26 |
|---|---|
| 3-{4-[N'-(3-Methyl-benzylidene)-hydrazino]-6-morpholin-4-yl-pyrimidin-2-yl}-propionic acid N'-phenyl-hydrazide | N-(3,4-Difluoro-benzyl)-N'-(2-{4-morpholin-4-yl-6-[N'-(3-trifluoromethyl-benzylidene)-hydrazino]-pyrimidin-2-yloxy}-ethyl)-guanidine |

Compound 41

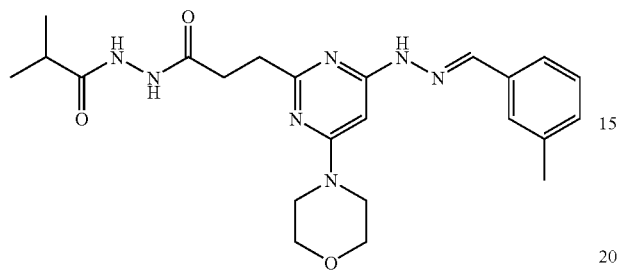

Isobutyric acid N'-(3-{4-[N'-(3-methyl-benzylidene)-hydrazino]-6-morpholin-4-yl-pyrimidin-2-yl}-propionyl)-hydrazide Compound 44

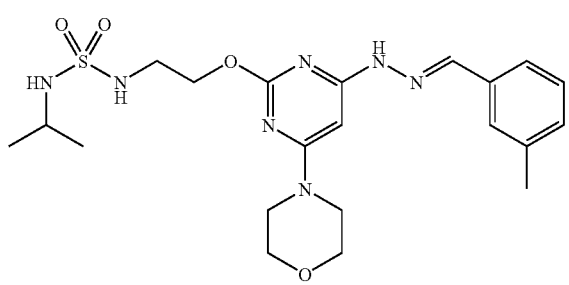

1-Isopropyl-3-(3-{4-[N'-(3-methyl-benzylidene)-hydrazino]-6-morpholin-4-yl-pyrimidin-2-yl}-propyl)-sulfamide Compound 42

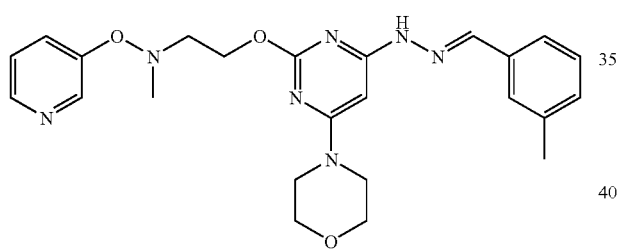

N-Methyl-N-(2-{4-[N'-(3-methyl-benzylidene)-hydrazino]-6-morpholin-4-yl-pyrimidin-2-yloxy}-ethyl)-O-pyridin-3-yl-hydroxylamine Compound 45

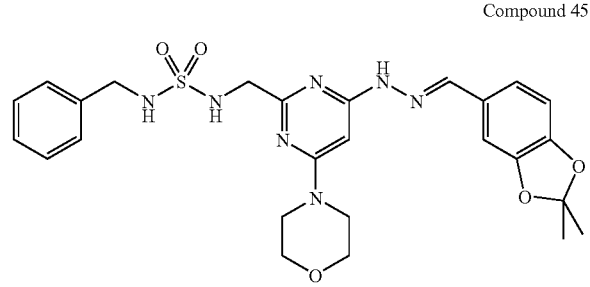

1-Benzyl-3-{4-[N'-(2,2-dimethyl-benzo[1,3]dioxol-5-ylmethylene)-hydrazino]-6-morpholin-4-yl-pyrimidin-2-ylmethyl}-sulfamide Compound 43

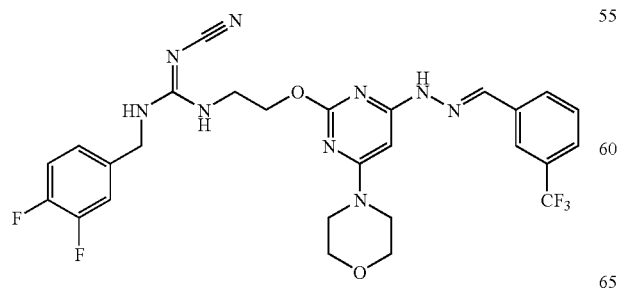

Compound 46

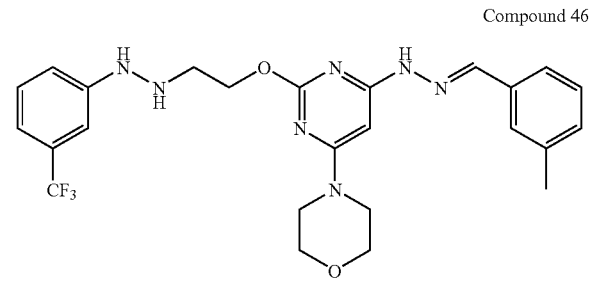

27

N-(3-Methyl-benzylidene)-N'-(6-morpholin-4-yl-2-{2-[N-(3-trifluoromethyl-phenyl)-hydrazino]-ethoxy}-pyrimidin-4-yl)-hydrazine

28

4-{4-[N'-(4-Chloro-benzylidene)-hydrazino]-6-morpholin-4-yl-pyrimidin-2-yloxymethyl}-N-(2-hydroxy-ethyl)-N-methyl-benzenesulfonamide

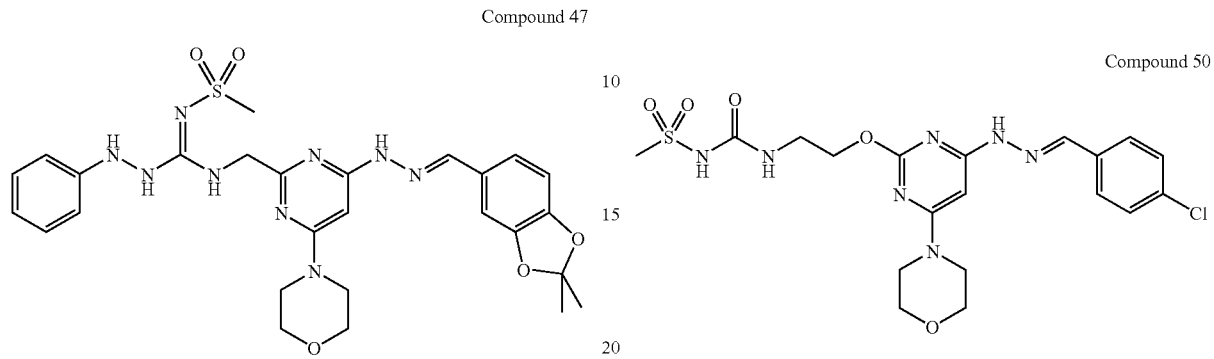

Compound 47

N-[({4-[N'-(2,2-Dimethyl-benzo[1,3]dioxol-5-ylmethylene)-hydrazino]-6-morpholin-4-yl-pyrimidin-2-ylmethyl}-amino)-(N'-phenyl-hydrazino)-methylene]-methanesulfonamide Compound 50

1-Methanesulfonyl-3-(2-{4-[N'-(4-chloro-benzylidene)-hydrazino]-6-morpholin-4-yl-pyrimidin-2-yloxy}-ethyl)-urea

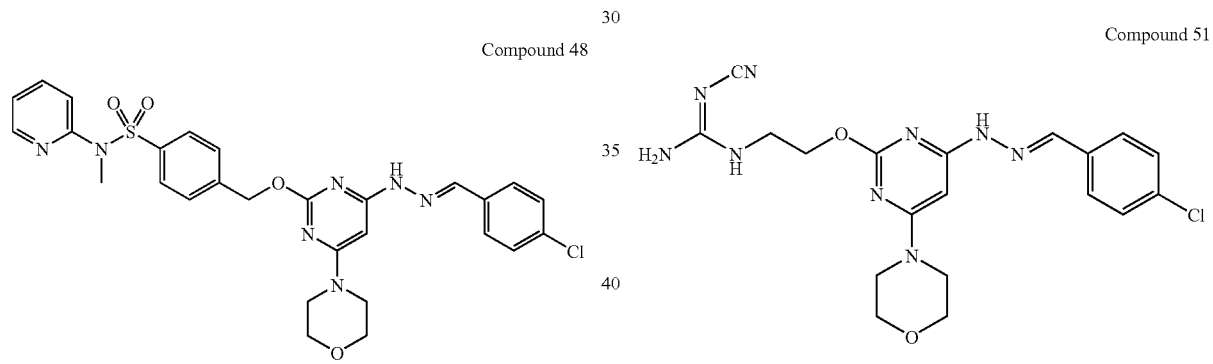

Compound 48

4-{4-[N'-(4-Chloro-benzylidene)-hydrazino]-6-morpholin-4-yl-pyrimidin-2-yloxymethyl}-N-methyl-N-pyridin-2-yl-benzenesulfonamide Compound 51

N-(2-{4-[N'-(4-Chloro-benzylidene)-hydrazino]-6-morpholin-4-yl-pyrimidin-2-yloxy}-ethyl)-cyanoguanidine

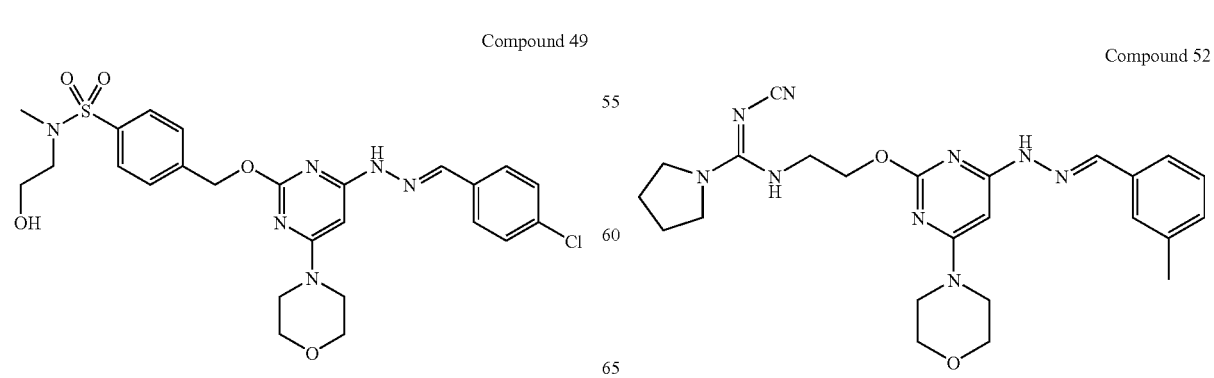

Compound 49

Compound 52

29

N-(2-{4-[N'-(3-Methyl-benzylidene)-hydrazino]-6-morpholin-4-yl-pyrimidin-2-yloxy}-ethyl)-pyrrolidine-1-(N-cyano)carboxamidine

30

Morpholine-4-carboxylic acid 2-{2-[N'-(3-methyl-benzylidene)-hydrazino]-6-morpholin-4-yl-pyrimidin-4-yloxy}-ethyl ester Compound 53

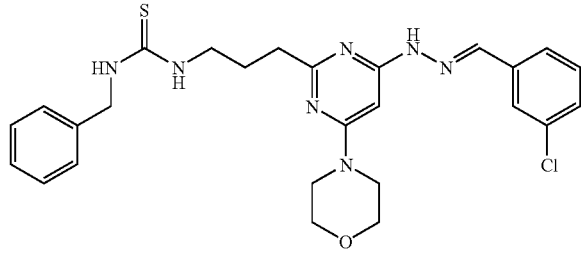

1-Benzyl-3-(3-{4-[N'-(3-chloro-benzylidene)-hydrazino]-6-morpholin-4-yl-pyrimidin-2-yl}-propyl)-thiourea Compound 56

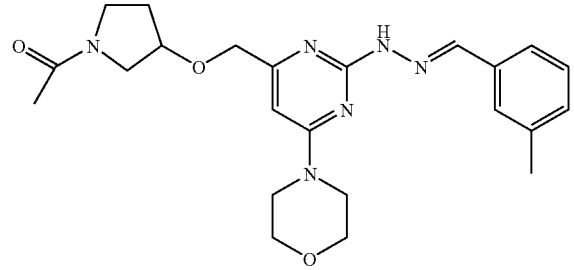

1-(3-{2-[N'-(3-Methyl-benzylidene)-hydrazino]-6-morpholin-4-yl-pyrimidin-4-ylmethoxy}-pyrrolidin-1-yl)-ethanone Compound 54

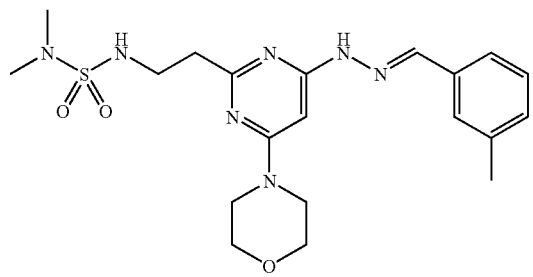

1,1-Dimethyl-3-(2-{4-[N'-(3-methyl-benzylidene)-hydrazino]-6-morpholin-4-yl-pyrimidin-2-yl}-ethyl)-sulfamide Compound 57

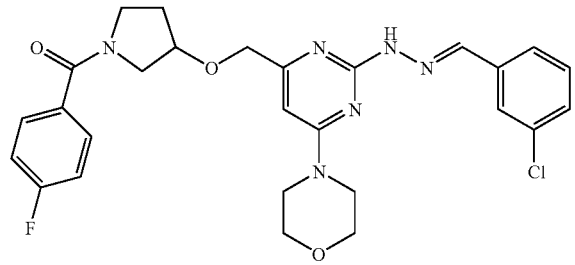

(3-{2-[N'-(3-Chloro-benzylidene)-hydrazino]-6-morpholin-4-yl-pyrimidin-4-ylmethoxy}-pyrrolidin-1-yl)-(4-fluoro-phenyl)-methanone Compound 55

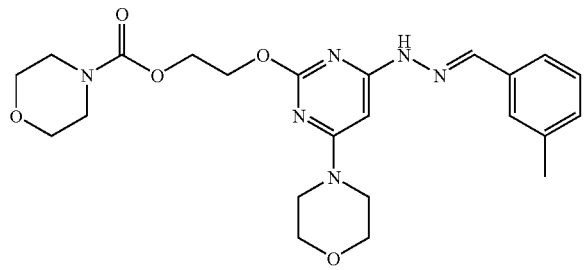

Compound 57

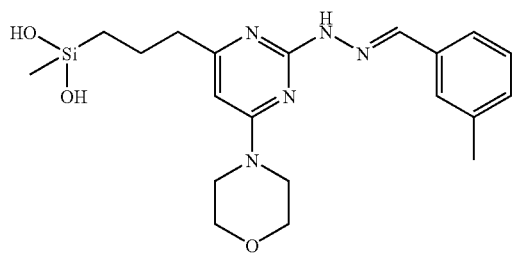

| 31 | 32 |
|---|---|
| Methyl-(3-{2-[N'-(3-methyl-benzylidene)-hydrazino]-6-morpholin-4-yl-pyrimidin-4-yl}-propyl)-silanediol | 4-{2-[N'-(3-Methyl-benzylidene)-hydrazino]-6-morpholin-4-yl-pyrimidin-4-yl}-propyl boronic acid |

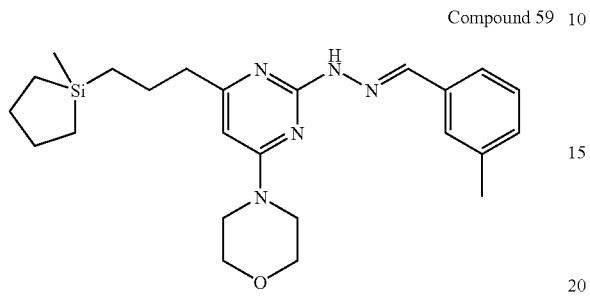

Compound 59

N-(3-Methyl-benzylidene)-N'-{4-[3-(1-methyl-silolan-1-yl)-propyl]-6-morpholin-4-yl-pyrimidin-2-yl}-hydrazine

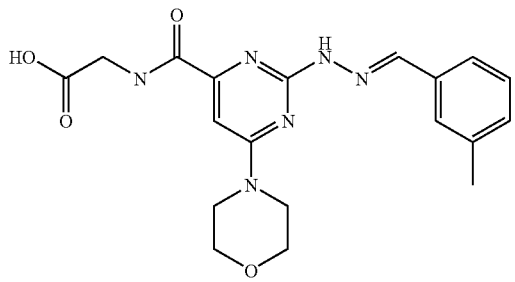

Compound 62

({2-[N'-(3-Methyl-benzylidene)-hydrazino]-6-morpholin-4-yl-pyrimidine-4-carbonyl}-amino)-acetic acid

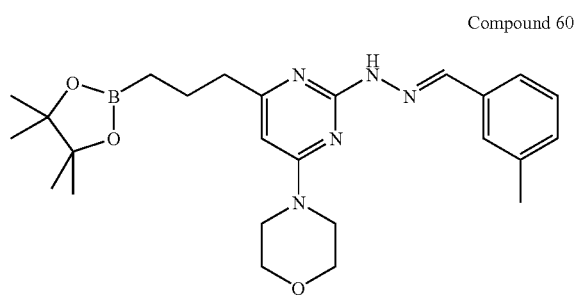

Compound 60

N-(3-Methyl-benzylidene)-N'-{4-morpholin-4-yl-6-[3-(4,4,5,5-tetramethyl-[1,3,2]dioxaborolan-2-yl)-propyl]-pyrimidin-2-yl}-hydrazine

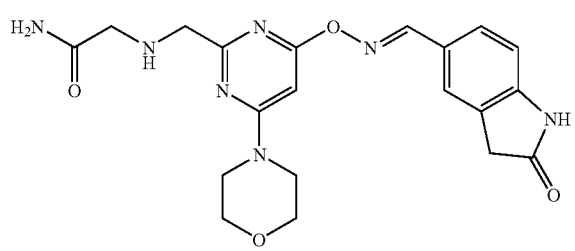

Compound 63

2-{[4-Morpholin-4-yl-6-(2-oxo-2,3-dihydro-1H-indol-5-ylmethyleneaminooxy)-pyrimidin-2-ylmethyl]-amino}-acetamide

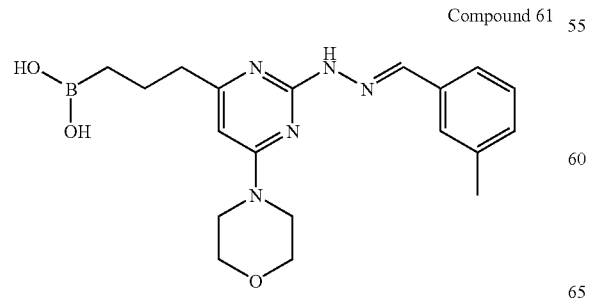

Compound 61

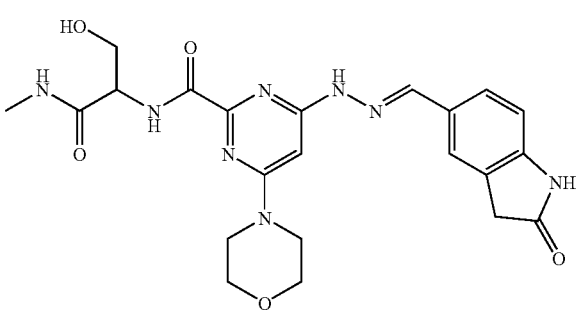

Compound 64

33

4-Morpholin-4-yl-6-[N'-(2-oxo-2,3-dihydro-1H-indol-5-ylmethylene)-hydrazino]-pyrimidine-2-carboxylic acid (2-hydroxy-1-methylcarbamoyl-ethyl)-amide

34

2-Amino-3-methyl-N-{4-morpholin-4-yl-6-[N'-(2-oxo-2,3-dihydro-1H-indol-5-ylmethylene)-hydrazino]-pyrimidin-2-ylmethyl}-butyramide Compound 65

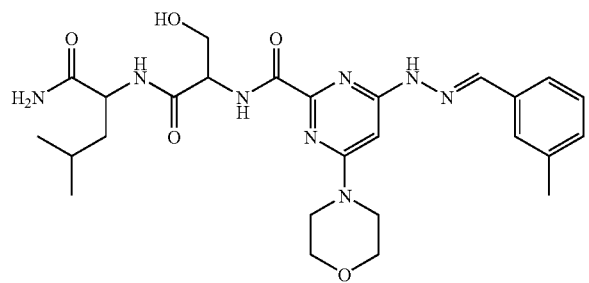

4-[N'-(3-Methyl-benzylidene)-hydrazino]-6-morpholin-4-yl-pyrimidine-2-carboxylic acid [1-(1-carbamoyl-3-methyl-butylcarbamoyl)-2-hydroxy-ethyl]-amide Compound 68

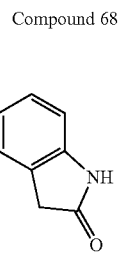

N-(1-Carbamoyl-ethyl)-3-{4-morpholin-4-yl-6-[N'-(2-oxo-2,3-dihydro-1H-indol-5-ylmethylene)-hydrazino]-pyrimidin-2-yl}-propionamide Compound 66

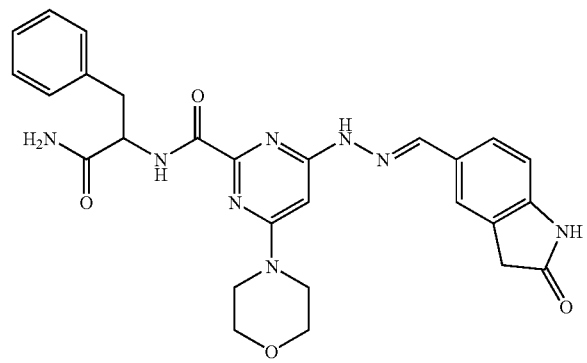

4-Morpholin-4-yl-6-[N'-(2-oxo-2,3-dihydro-1H-indol-5-ylmethylene)-hydrazino]-pyrimidine-2-carboxylic acid (1-carbamoyl-2-phenyl-ethyl)-amide Compound 69

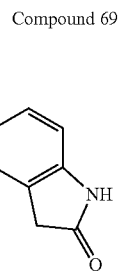

4-Morpholin-4-yl-6-[N'-(2-oxo-2,3-dihydro-1H-indol-5-ylmethylene)-hydrazino]-pyrimidine-2-carboxylic acid (2-morpholin-4-yl-2-oxo-ethyl)-amide Compound 67

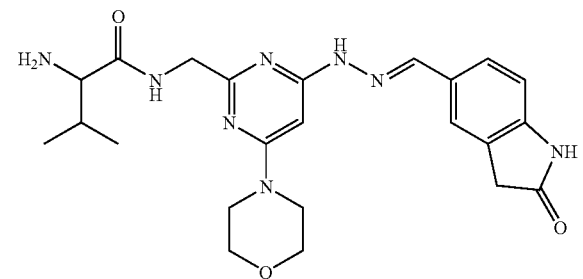

Compound 70

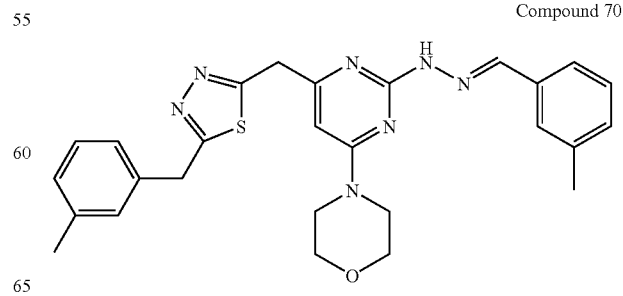

35

N-(3-Methyl-benzylidene)-N'-{4-[5-(3-methyl-benzyl)-[1,3,4]thiadiazol-2-ylmethyl]-6-morpholin-4-yl-pyrimidin-2-yl}-hydrazine

36

1-(2-{4-Morpholin-4-yl-6-[N'-(2-oxo-2,3-dihydro-1H-indol-5-ylmethylene)-hydrazino]-pyrimidin-2-yl}-ethyl)-1H-[1,2,3]triazole-4-carboxylic acid dimethylamide

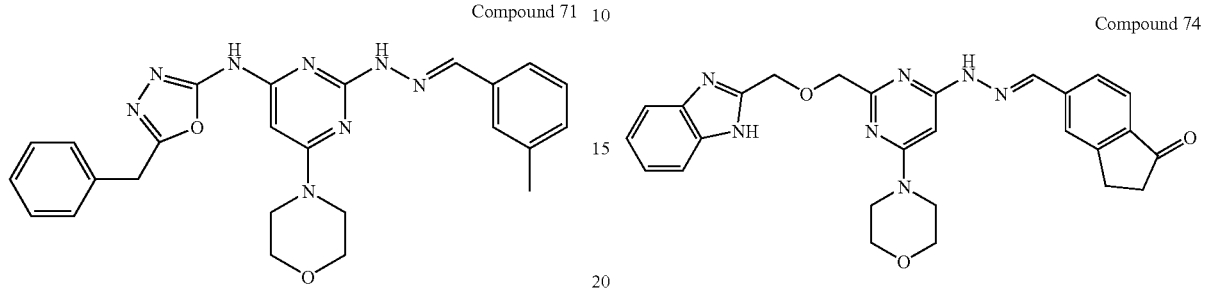

Compound 71

(5-Benzyl-[1,3,4]oxadiazol-2-yl)-{2-[N'-(3-methyl-benzylidene)-hydrazino]-6-morpholin-4-yl-pyrimidin-4-yl}-amine Compound 74

5-{[2-(1H-Benzoimidazol-2-ylmethoxymethyl)-6-morpholin-4-yl-pyrimidin-4-yl]-hydrazonomethyl}-indan-1-one

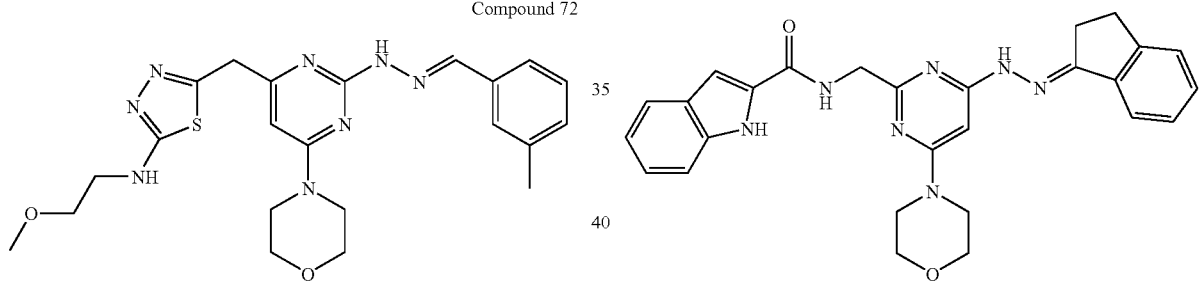

Compound 72

(2-Methoxy-ethyl)-(5-{2-[N'-(3-methyl-benzylidene)-hydrazino]-6-morpholin-4-yl-pyrimidin-4-ylmethyl}-[1,3,4]thiadiazol-2-yl)-amine Compound 75

1H-Indole-2-carboxylic acid [4-(N'-indan-1-ylidene-hydrazino)-6-morpholin-4-yl-pyrimidin-2-ylmethyl]-amide

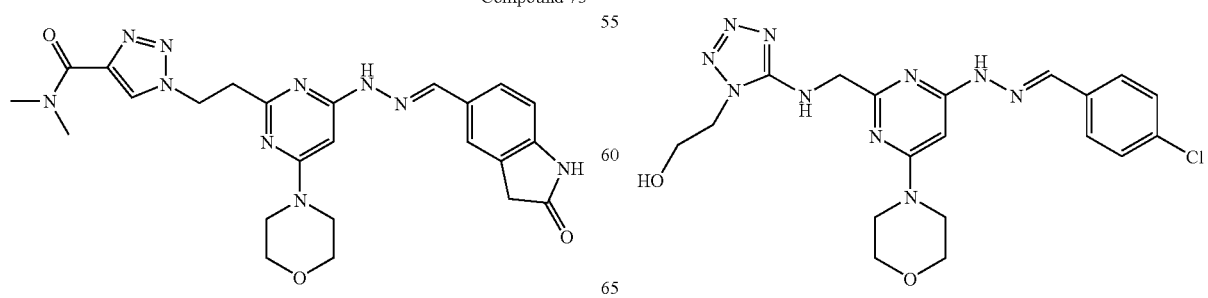

Compound 73

Compound 76

| 37 | 38 |
|---|---|
| 2-[5-({4-[N'-(4-Chloro-benzylidene)-hydrazino]-6-morpholin-4-yl-pyrimidin-2-ylmethyl}-amino)-tetrazol-1-yl]-ethanol | 4-{4-[N'-(2,2-Dimethyl-benzo[1,3]dioxol-5-ylmethylene)-hydrazino]-6-morpholin-4-yl-pyrimidin-2-ylmethyl}-piperazine-1-sulfonic acid dimethylamide |

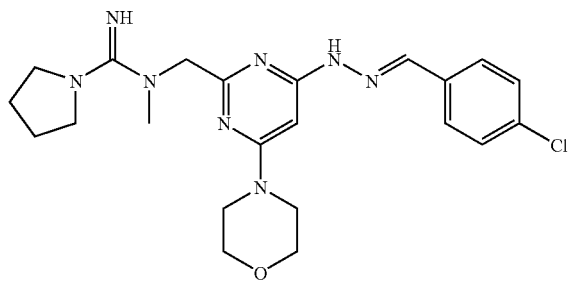

Compound 77

N-{4-[N'-(4-Chloro-benzylidene)-hydrazino]-6-morpholin-4-yl-pyrimidin-2-ylmethyl}-N-methyl-pyrrolidine-1-carboxamidine; compound with methane

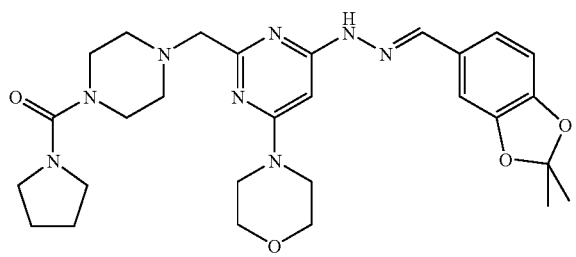

Compound 80

(4-{4-[N'-(2,2-Dimethyl-benzo[1,3]dioxol-5-ylmethylene)-hydrazino]-6-morpholin-4-yl-pyrimidin-2-ylmethyl}-piperazin-1-yl)-pyrrolidin-1-yl-methanone

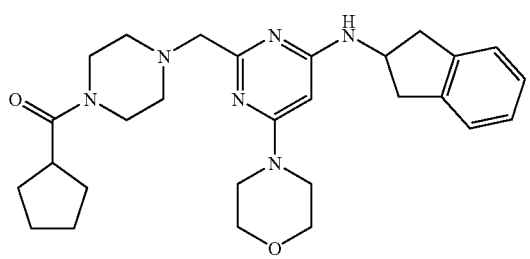

Compound 78

Cyclopentyl-{4-[4-(indan-2-ylamino)-6-morpholin-4-yl-pyrimidin-2-ylmethyl]-piperazin-1-yl}-methanone

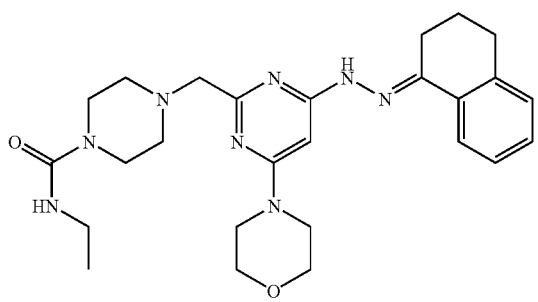

Compound 81

4-{4-[N'-(3,4-Dihydro-2H-naphthalen-1-ylidene)-hydrazino]-6-morpholin-4-yl-pyrimidin-2-ylmethyl}-piperazine-1-carboxylic acid ethylamide

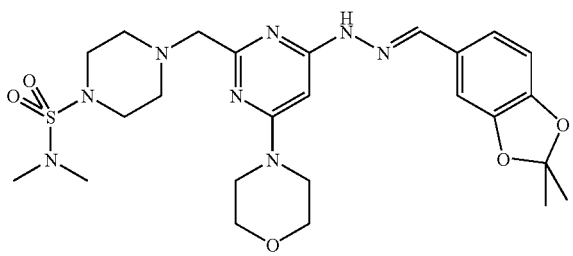

Compound 79

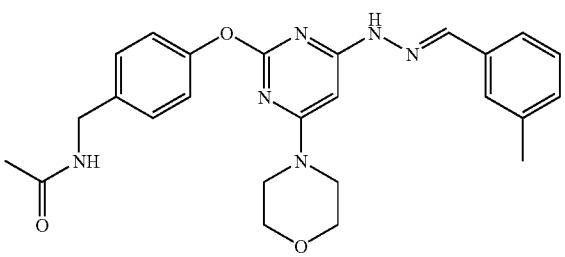

Compound 82

| 39 | 40 |
|---|---|
| N-(4-{4-[N'-(3-Methyl-benzylidene)-hydrazino]-6-morpholin-4-yl-pyrimidin-2-yloxy}-benzyl)-acetamide | Dimethyl-carbamic acid 2-{2-[N'-(3-methyl-benzylidene)-hydrazino]-6-morpholin-4-yl-pyrimidin-4-yloxy}-ethyl ester |

Compound 83

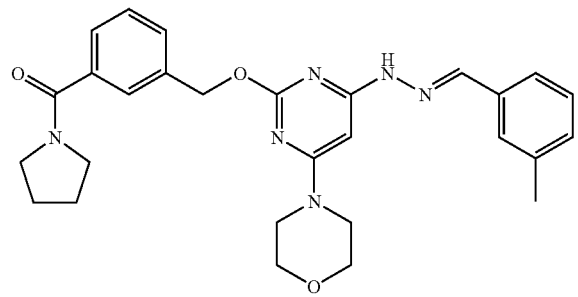

(4-Cyclopentyloxymethyl-phenyl)-{4-[N'-(3-methyl-benzylidene)-hydrazino]-6-morpholin-4-yl-pyrimidin-2-yl}-amine Compound 84

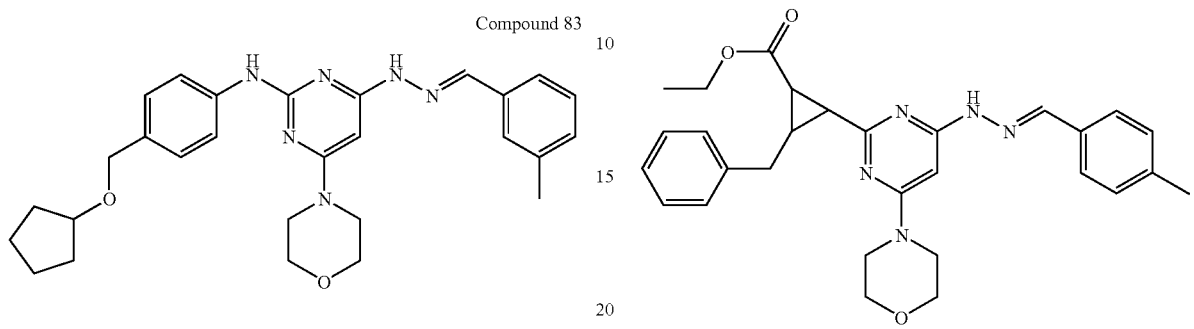

(3-{4-[N'-(3-Methyl-benzylidene)-hydrazino]-6-morpholin-4-yl-pyrimidin-2-yloxymethyl}-phenyl)-pyrrolidin-1-yl-methanone Compound 85

Compound 86

2-Benzyl-3-{4-[N'-(4-methyl-benzylidene)-hydrazino]-6-morpholin-4-yl-pyrimidin-2-yl}-cyclopropanecarboxylic acid ethyl ester Compound 87

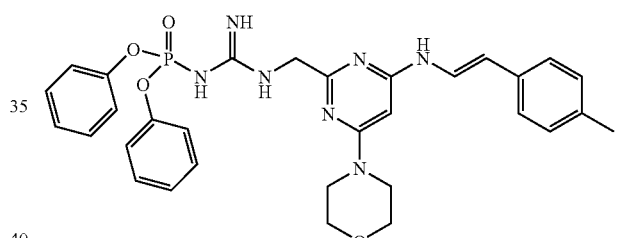

Compound 88

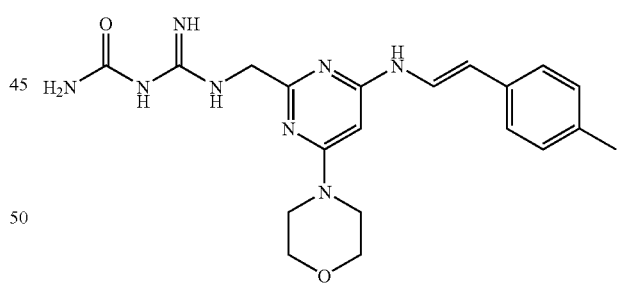

Compound 89

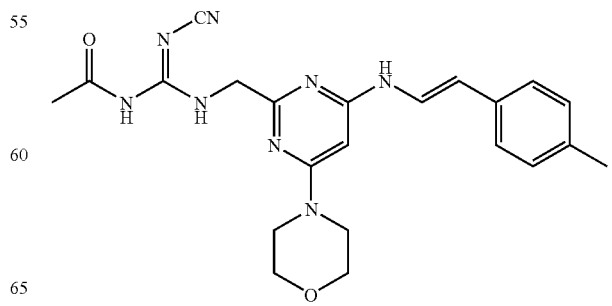

-continued

Compound 90

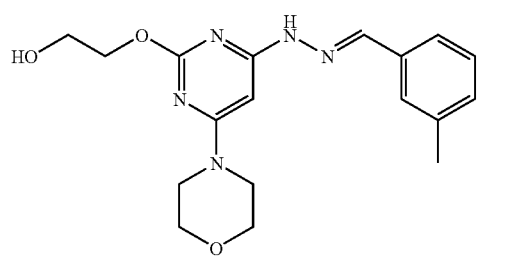

2-{4-[N'-(3-Methyl-benzylidene)-hydrazino]-6-morpholin-4-yl-pyrimidin-2-yloxy}-ethanol Compound 91

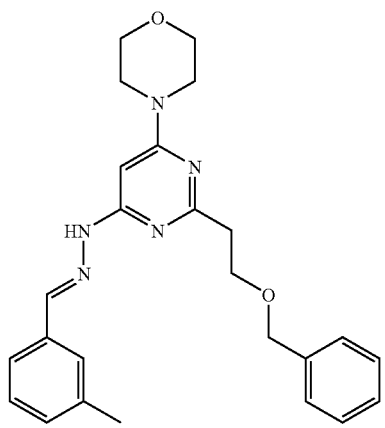

N-[2-(2-benzyloxy-ethyl)-6-morpholin-4-yl-pyrimidin-4-yl]-N'-(3-methyl-benzylidene)-hydrazine Compound 92

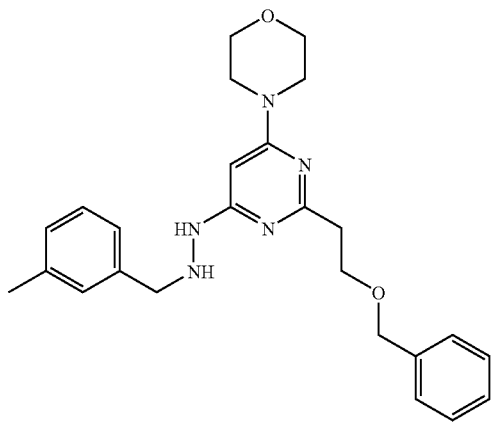

N-[2-(2-benzyloxy-ethyl)-6-morpholin-4-yl-pyrimidin-4-yl]-N'-(3-methyl-benzyl)-hydrazine Compound 93

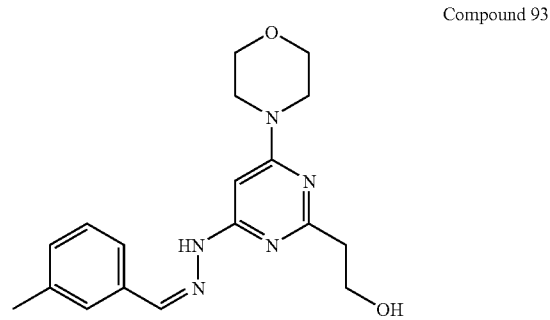

2-{4-[N'-(3-methyl-benzylidene)-hydrazino]-6-morpholin-4-yl-pyrimidin-2-yl}-ethanol Compound 94

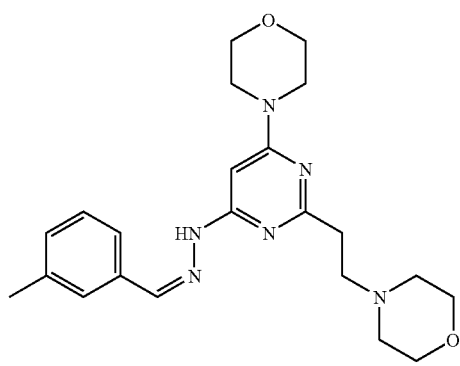

N-(3-methyl-benzylidene)-N'-[6-morpholin-4-yl-2-(2-morpholin-4-yl-ethyl)-pyrimidin-4-yl]-hydrazine Compound 95

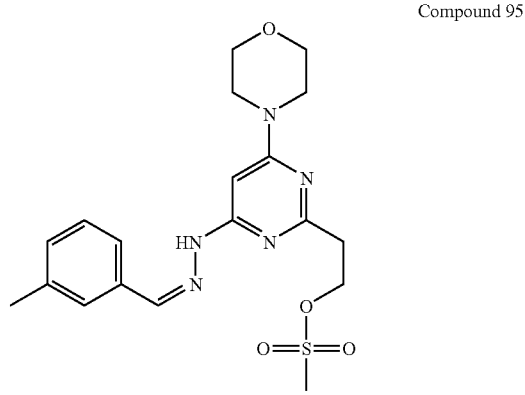

| 43 | 44 |
|---|---|
| methanesulfonic acid 2-{4-[N'-(3-methyl-benzylidene)-hydrazino]-6-morpholin-4-yl-pyrimidin-2-yl}-ethyl ester | 2-methyl-4-{4-[N'-(3-methyl-benzylidene)-hydrazino]-6-morpholin-4-yl-pyrimidin-2-yl}-butan-2-ol |

Compound 96

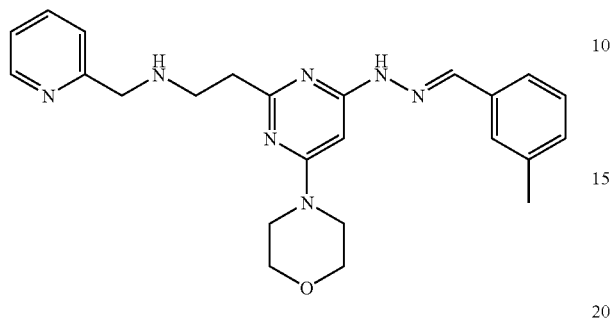

(2-{4-[N'-(3-Methyl-benzylidene)-hydrazino]-6-morpholin-4-yl-pyrimidin-2-yl}-ethyl)-pyridin-2-ylmethyl-amine Compound 99

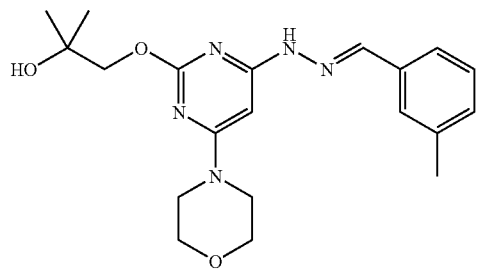

2-Methyl-1-{4-[N'-(3-methyl-benzylidene)-hydrazino]-6-morpholin-4-yl-pyrimidin-2-yloxy}-propan-2-ol Compound 97

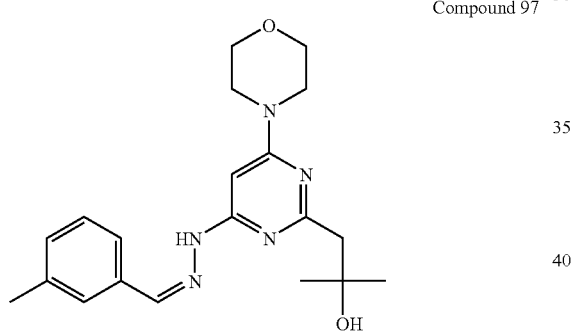

2-methyl-1-{4-[N'-(3-methyl-benzylidene)-hydrazino]-6-morpholin-4-yl-pyrimidin-2-yl}-propan-2-ol Compound 100

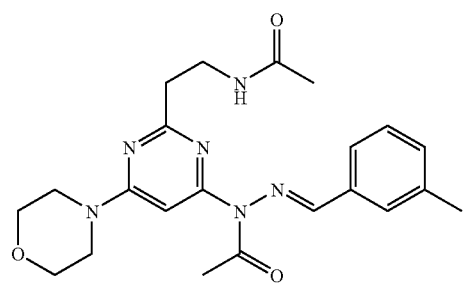

N-(2-{4-[N-Acetyl-N'-(3-methyl-benzylidene)-hydrazino]-6-morpholin-4-yl-pyrimidin-2-yl}-ethyl)-acetamide Compound 98

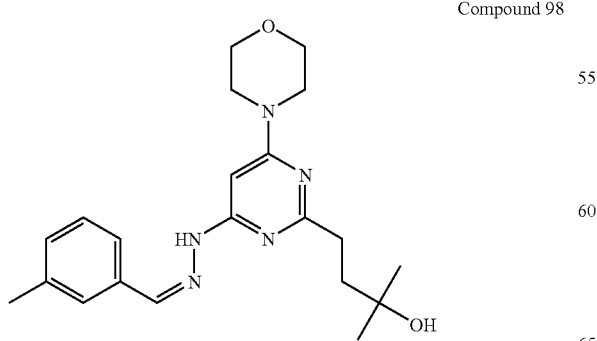

Compound 101

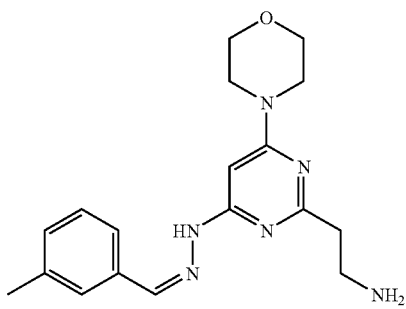

2-{4-[N'-(3-methyl-benzylidene)-hydrazino]-6-morpholin-4-yl-pyrimidin-2-yl}-ethylamine

Propyl-carbamic acid 2-{2-[N'-(3-methyl-benzylidene)-hydrazino]-6-morpholin-4-yl-pyrimidin-4-yloxy}-ethyl ester

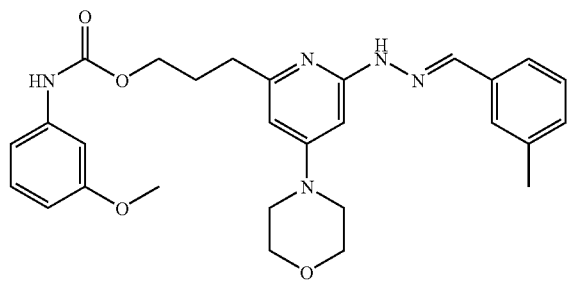

Compound 102

(3-methoxy-phenyl)-carbamic acid 3-{4-[N'-(3-methyl-benzylidene)-hydrazino]-6-morpholin-4-yl-pyrid-2-yl}-propyl ester Compound 105

(4-Methoxy-benzyl)-carbamic acid 2-{2-[N'-(3-methyl-benzylidene)-hydrazino]-6-morpholin-4-yl-pyrimidin-4-yloxy}-ethyl ester

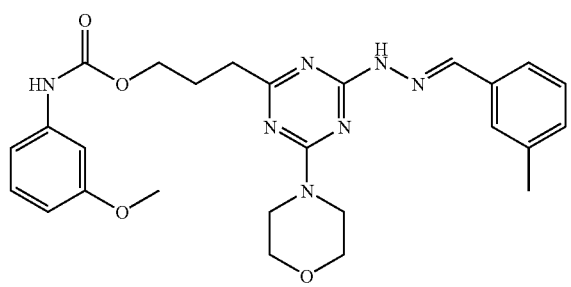

Compound 103

(3-methoxy-phenyl)-carbamic acid 3-{4-[N'-(3-methyl-benzylidene)-hydrazino]-6-morpholin-4-yl-triazin-2-yl}-propyl ester Compound 106

Pyridin-3-yl-carbamic acid 2-{4-[N'-(3-methyl-benzylidene)-hydrazino]-6-morpholin-4-yl-pyrimidin-2-yloxy}-ethyl ester

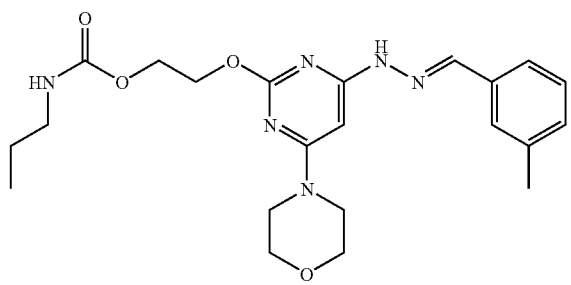

Compound 104

The heterocyclic compounds of this invention include the compounds themselves, as well as their salts and their prodrugs, if applicable. Such salts, for example, can be formed between a positively charged substituent (e.g., amino) on a compound and an anion. Suitable anions include, but are not limited to, chloride, bromide, iodide, sulfate, nitrate, phosphate, citrate, methanesulfonate, trifluoroacetate, and acetate. Likewise, a negatively charged substituent (e.g., carboxylate) on a compound can form a salt with a cation. Suitable cations include, but are not limited to, sodium ion, potassium ion, magnesium ion, calcium ion, and an ammonium cation such as teteramethylammonium ion. Examples of prodrugs include esters and other pharmaceutically acceptable derivatives, which, upon administration to a subject, are capable of providing the heterocyclic compounds described above in vivo (see Goodman and Gilman's, The Pharmacological basis of Therapeutics, $8^{th}$ ed., McGraw-Hill, Int. Ed. 1992, "Biotransformation of Drugs").

In addition, some of the heterocyclic compounds of this invention have one or more double bonds, or one or more asymmetric centers. Such compounds can occur as racemates, racemic mixtures, single enantiomers, individual diastereomers, diastereomeric mixtures, and cis- or trans- or E- or Z-double isomeric forms. All such isomeric forms of these compounds are expressly included in the present invention. The compounds of this invention may also be represented in multiple tautomeric forms, in such instances, the invention expressly includes all tautomeric forms of the compounds described herein (e.g., alkylation of a ring system may result in alkylation at multiple sites, the invention expressly includes all such reaction products). All such isomeric forms of such compounds are expressly included in the present invention. All crystal forms of the compounds described herein are expressly included in the present invention.

Further, the aforementioned heterocyclic compounds also include their N-oxides. The term "N-oxides" refers to one or more nitrogen atoms, when present in a heterocyclic compound, are in N-oxide form, i.e., N→O.

The compounds described herein can be prepared by methods well known in the art, as well as by the synthetic routes disclosed herein. For example, a pyrimidine compound can be prepared by using 2,4,6-trichloro-pyrimidine as a starting material. The three chloro groups can be displaced by various substitutes. More specifically, a first chloro group (e.g., at position 6) can react with, e.g., morpholine, to form a morpholinyl pyrimidine. 2-Aryl and 2-alkylpyrimidine dichloro compounds can also be prepared by reacting an amidine with a malonic ester followed by treatment with phosphorous oxychloride. A second chloro group can be replaced by reacting with a nucleophile, such as an alcohol in the presence of base, e.g., sodium hydride. In other examples, a compound of formula (I), wherein Y is $CH_2$ can be prepared by reacting the pyrimidine chloride with a Grignard reagent, an organotin reagent, an organocopper reagent, an organoboric acid, or an organozinc reagent in the presence of an organopalladium compound as a catalyst. Isomeric forms may be produced. The desired isomeric product can be separated from others by, e.g., high performance liquid chromatography. A third chloro group can undergo a displacement reaction with, e.g., hydrazine, and the primary amine of the coupled hydrazine moiety further reacts with an aldehyde, e.g., indole-3-carboxaldehyde to form a hydrazone linkage. Thus, a pyrimidine compound of this invention is obtained. If preferred, other types of linkages can be prepared by similar reactions. Sensitive moieties on a pyrimidinyl intermediate and a nucleophile can be protected prior to coupling. The chemicals used in the above-described synthetic routes may include, for example, solvents, reagents, catalysts, and protecting group and deprotecting group reagents. The methods described above may also additionally include steps, either before or after the steps described specifically herein, to add or remove suitable protecting groups in order to ultimately allow synthesis of the heterocyclic compounds. In addition, various synthetic steps may be performed in an alternate sequence or order to give the desired compounds. Synthetic chemistry transformations and protecting group methodologies (protection and deprotection) useful in synthesizing applicable heterocyclic compounds are known in the art and include, for example, those described in R. Larock, *Comprehensive Organic Transformations*, VCH Publishers (1989); T. W. Greene and P. G. M. Wuts, *Protective Groups in Organic Synthesis*, 3$^{rd}$ Ed., John Wiley and Sons (1999); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof.

Correspondingly, pyridinyl and triazinyl compounds described herein can be made according to methods know in the art, including those in the aforementioned treatises. The pyridinyl and triazinyl compounds can be made using analogous synthetic procedures and reagents as described for the pyrimidinyl compounds. It is recognized by one of ordinary skill that pyrimidines demonstrate reactivity intermediate relative to that of pyridines and triazines, therefore reaction conditions (e.g., temperature, reaction time, etc.) may be adjusted accordingly, which is routine for one of ordinary skill.

A heterocyclic compound thus obtained can be further purified by flash column chromatography, high performance liquid chromatography, or crystallization.

Also within the scope of this invention is a pharmaceutical composition that contains one or more of the heterocyclic compounds of this invention (including an effective amount of the compound(s)) and a pharmaceutically acceptable carrier. Further, the present invention covers a method of administering an effective amount of such a compound to a subject in need of treatment of IL-12 overproduction related diseases (e.g., rheumatoid arthritis, sepsis, Crohn's disease, multiple sclerosis, psoriasis, or insulin-dependent diabetes mellitus). "An effective amount" refers to the amount of the compound which is required to confer a therapeutic effect on the treated subject. The interrelationship of dosages for animals and humans (based on milligrams per meter squared of body surface) is described in Freireich et al., (1966) *Cancer Chemother Rep* 50: 219. Body surface area may be approximately determined from height and weight of the patient. See, e.g., Scientific Tables, Geigy Pharmaceuticals, Ardley, N.Y., 1970, 537. An effective amount of the heterocyclic compound of this invention can range from about 0.001 mg/Kg to about 1000 mg/Kg, more preferably 0.01 mg/Kg to about 100 mg/Kg. Effective doses will also vary, as recognized by those skilled in the art, depending on the diseases treated, route of administration, excipient usage, and the possibility of co-usage with other therapeutic treatments such as use of other agents.

To practice the method of the present invention, a heterocyclic compound, as a component of a pharmaceutical composition, can be administered orally, parenterally, by inhalation spray, topically, rectally, nasally, buccally, vaginally or via an implanted reservoir. The term "parenteral" as used herein includes subcutaneous, intracutaneous, intravenous, intramuscular, intraarticular, intraarterial, intrasynovial, intrasternal, intrathecal, intralesional and intracranial injection or infusion techniques.

A sterile injectable composition, for example, a sterile injectable aqueous or oleaginous suspension, can be formulated according to techniques known in the art using suitable dispersing or wetting agents (such as, for example, Tween 80) and suspending agents. The sterile injectable preparation can also be a sterile injectable solution or suspension in a non-toxic parenterally acceptable diluent or solvent, for example, as a solution in 1,3-butanediol. Among the acceptable vehicles and solvents that can be employed are mannitol, water, Ringer's solution and isotonic sodium chloride solution. In addition, sterile, fixed oils are conventionally employed as a solvent or suspending medium (e.g., synthetic mono- or diglycerides). Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions can also contain a long-chain alcohol diluent or dispersant, or carboxymethyl cellulose or similar dispersing agents. Other commonly used surfactants such as Tweens or Spans or other similar emulsifying agents or bioavailability enhancers which are commonly used in the manufacture of pharmaceutically acceptable solid, liquid, or other dosage forms can also be used for the purposes of formulation.

A composition for oral administration can be any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added. A nasal aerosol or inhalation composition can be prepared according to techniques well-known in the art of pharmaceutical formulation and can be prepared as solutions in saline, employing benzyl alcohol or other suitable preservatives, absorption promoters to enhance bioavailability, fluorocarbons, and/or other solubilizing or dispersing agents known in the art. A heterocyclic compound of this invention can also be administered in the form of suppositories for rectal administration.

The carrier in the pharmaceutical composition must be "acceptable" in the sense of being compatible with the active ingredient of the formulation (and preferably, capable of stabilizing it) and not deleterious to the subject to be treated. For example, solubilizing agents such as cyclodextrins, which form specific, more soluble complexes with the compounds of this invention, or one or more solubilizing agents, can be utilized as pharmaceutical excipients for delivery of the heterocyclic compounds. Examples of other carriers include colloidal silicon dioxide, magnesium stearate, cellulose, sodium lauryl sulfate, and D&C Yellow # 10.

As used herein, the terms "animal", "subject" and "patient", include, but are not limited to, a cow, monkey, horse, sheep, pig, chicken, turkey, quail, cat, dog, mouse, rat, rabbit, guinea pig and human (preferably, a human).

As used herein, the term "pharmaceutically acceptable solvate," is a solvate formed from the association of one or more solvent molecules to one of the compounds of formula (I). The term solvate includes hydrates (e.g., mono-hydrate, dihydrate, trihydrate, tetrahydrate, and the like).

The biological activities of a heterocyclic compound can be evaluated by a number of cell-based assays. One of such assays can be conducted using cells from human peripheral blood mononuclear cells (PBMC) or human monocytic cell line (THP-1). The cells are stimulated with a combination of human interferon-γ (IFNγ) and lipopolysaccharide or a combination of IFNγ and *Staphylococcus aureus* Cowan I in the presence of a test compound. The level of inhibition of IL-12 production can be measured by determining the amount of p70 by using a sandwich ELISA assay with anti-human IL-12 antibodies. $IC_{50}$ of the test compound can then be determined. Specifically, PBMC or THP-1 cells are incubated with the test compound. Cell viability was assessed using the bioreduction of MTS [3-(4,5-dimethylthiazol-2-yl)-5-(3-carboxymethoxyphenyl)-2-(4-sulfophenyl)-2H-tetrazolium] (Promega, Madison, Wis.).

A heterocyclic compound can also be evaluated by animal studies. For example, one of such studies involves the ability of a test compound to treat adjuvant arthritis (i.e., a IL-12 overproduction related disorder) in rats.

Without further elaboration, it is believed that the above description has adequately enabled the present invention. The following specific embodiments are, therefore, to be construed as merely illustrative, and not limitative of the remainder of the disclosure in any way whatsoever. All of the references and publications cited herein are hereby incorporated by reference in their entirety.

EXAMPLE 1

Synthesis of Compound 1

2-Methyl-4,6-dihydroxy pyrimidine (42.0 g.; 333 mmol) was added to phosphoryl chloride (350 mL). The reaction mixture was heated at reflux for three hours. The solvent was removed under reduced pressure until the volume was approximately 100 mL, and the reaction mixture was then poured onto ice (500 mL) and stirred for ten minutes. Dichloromethane (200 mL) was added, and after shaking, the organic layer was dried with sodium sulfate and evaporated to yield crude S1; 2-methyl-4,6-dichloropyrimidine (41.8 g.; 256 mmol).

The crude S1; 2-methyl-4,6-dichloropyrimidine (41.8 g.; 256 mmol) was dissolved in dichloromethane (200 mL) and chilled to –78° C. in an inert atmosphere. Morpholine (48 g.; 550 mol) dissolved in dichloromethane (100 mL) was added slowly. The reaction was allowed to warm to room temperature while stirring overnight. The organic layer was washed with saturated ammonium chloride (2×100 mL), dried with sodium sulfate, and evaporated to give S2; 2-methyl-4-chloro-6-morpholino-pyrimidine (48.5 g.; 227 mmol).

S2; 2-methyl-4-chloro-6-morpholino-pyrimidine (10.7 g.; 50 mmol) was dissolved in tetrahydrofuran (200 mL). The reaction was chilled to –78° C. under an inert atmosphere. A solution of n-butyllithium in hexanes (24 mL, 2.5M, 60 mmol) was added, and the reaction mixture was stirred for thirty minutes. A solution of oxirane dissolved in tetrahydrofuran (40 mL, 41.5M, 60 mmol) was added, and the reaction was allowed to warm to room temperature while stirring overnight. The solvent was removed under reduced pressure, and the crude material was dissolved in methylene chloride (200 mL) and washed with saturated ammonium chloride (2×50 mL), dried with sodium sulfate, and evaporated to dryness. The compound was purified by column chromatography to give S3; 3-(4-chloro-6-morpholin-4-yl-pyrimidin-2-yl)-propan-1-ol (6.6 g., 25.6 mmol).

S3; 3-(4-Chloro-6-morpholin-4-yl-pyrimidin-2-yl)-propan-1-ol (5.0 g., 19.4 mmol) was dissolved in dioxane (30 mL). To the reaction mixture was added anhydrous hydrazine (10 mL, 300 mmol). The reaction was then heated at reflux for five hours. The solvent was removed under reduced pressure, and the crude solid was dissolved in a mixture of dichloromethane (800 mL) and 10% potassium carbonate (40 mL). The organic layer was isolated, dried with sodium sulfate, and evaporated to yield crude S4; 3-(4-hydrazino-6-morpholin-4-yl-pyrimidin-2-yl)-propan-1-ol (4.3 g., 17 mmol).

S4; 3-(4-hydrazino-6-morpholin-4-yl-pyrimidin-2-yl)-propan-1-ol (4.3 g., 17 mmol) was dissolved in ethanol (40 mL). To the mixture was added m-tolylaldehyde (2.15 g., 18 mmol) and one drop of glacial acetic acid. The reaction was heated at 50° C. for one hour, and then cooled to room temperature. The precipitate was filtered, washed with ethanol (10 mL) and dried in vacuo to give S5; 3-{4-[N'-(3-methyl-benzylidene)-hydrazino]-6-morpholin-4-yl-pyrimidin-2-yl}-propan-1-ol (5.0 g., 14 mmol) as a white powder.

S5; 3-{4-[N'-(3-methyl-benzylidene)-hydrazino]-6-morpholin-4-yl-pyrimidin-2-yl}-propan-1-ol (355 mg, 1 mmol) was dissolved in acetonitrile (4 mL). To the mixture was added m-methoxyphenylisocyanate (149 mg., 1 mmol) and a catalytic amount of dimethylaminopyridine. The reaction was stirred at 60° C. for 16 hours. The reaction was then cooled to 4° C., and the precipitate was filtered, washed with acetonitrile (1 mL) and dried to give Compound 1, (3-methoxy-phenyl)-carbamic acid 3-{4-[N'-(3-methyl-benzylidene)-hydrazino]-6-morpholin-4-yl-pyrimidin-2-yl}-propyl ester.

Compound 2 was prepared in an analogous fashion to Compound 1 as described above except that m-trifluoromethylphenylisocyanate was used instead of m-methoxyphenylisocyanate.

Compound 3 was prepared in an analogous fashion to Compound 1 as described above except that p-methylphenylisocyanate was used instead of m-methoxyphenylisocyanate.

Compound 4 was synthesized in an analogous fashion to Compound 1 as described above except that m-trifluoromethylphenylisocyanate was used instead of m-methoxyphenylisocyanate. In addition, the relevant precursor was synthesized in an analogous fashion to S4 except that methylhydrazine was used in place of hydrazine.

Compound 14 was prepared in an analogous fashion to Compound 4 as described above except that p-tolylisocyanate was used instead of m-trifluoromethylphenylisocyanate.

Compound 5 was prepared in an analogous fashion to Compound 1 as described above except that cyclohexylisocyanate was used instead of m-methoxyphenylisocyanate.

Compound 6 was prepared in an analogous fashion to Compound 1 as described above except that o-fluorophenylisocyanate was used instead of m-methoxyphenylisocyanate.

Compound 7 was prepared in an analogous fashion to Compound 1 as described above except that p-nitrophenylisocyanate was used instead of m-methoxyphenylisocyanate.

Compound 8 was prepared in an analogous fashion to Compound 1 as described above except that ethylisocyanate was used instead of m-methoxyphenylisocyanate.

Compound 9 was prepared in an analogous fashion to Compound 1 as described above, with the substrate 3-isothiocyanatopyridine reacting in an analogous fashion to the aryl isocyanates described above.

Compound 10 was prepared in an analogous fashion to Compound 1 as described above except that 1-naphthyl isocyanate was used instead of m-methoxyphenylisocyanate.

Compound 11 was prepared in an analogous fashion to Compound 1 as described above except that p-phenoxyphenylisocyanate was used instead of m-methoxyphenylisocyanate.

Compound 13 was prepared in an analogous fashion to Compound 1 as described above.

Compound 19 was prepared in an analogous fashion to the last step of the synthesis of Compound 1 as described above, except Compound 90, 2-(4-chloro-6-morpholin-4-yl-pyrimidin-2-yloxy)-ethanol was reacted with the p-methylphenylisocyanate. Compound 90 was prepared in analogous fashion to Compound 99, except that ethylene glycol was used as the alcohol.

Compound 104 was made in an analogous fashion to Compound 1 as described above except that propylisocyanate was used instead of m-methoxyphenylisocyanate.

Compound 105 was made in an analogous fashion to Compound 1 as described above except that p-methoxybenzylisocyanate was used instead of m-methoxyphenylisocyanate.

Compound 106 was made in an analogous fashion to Compound 1 as described above except that 3-pyridyl isocyanate was used instead of m-methoxyphenylisocyanate.

EXAMPLE 2

Synthesis of Compound 91

S2; 2-methyl-4-chloro-6-morpholino-pyrimidine (10.7 g.; 50 mmol) was dissolved in tetrahydrofuran (200 mL). To the reaction mixture was added diisopropylamine (1 mL, 10 mmol). The reaction was chilled to −78° C. under an inert atmosphere. A solution of n-butyllithium in hexanes (24 mL, 2.5M, 60 mmol) was added, and the reaction mixture was stirred for thirty minutes. To the reaction was added benzyloxymethyl chloride (9.4 g., 60 mmol) and the reaction was allowed to warm to room temperature while stirring overnight. The solvent was removed under reduced pressure, and the crude material was dissolved in methylene chloride (200 mL) and washed with saturated ammonium chloride (2×50 mL), dried with sodium sulfate, and evaporated to dryness. The compound was purified by column chromatography to give S6, 4-(2-benzyloxymethyl-6-chloro-pyrimidin-4-yl)-morpholine (11.28 g., 33.8 mmol).

S6, 4-(2-benzyloxymethyl-6-chloro-pyrimidin-4-yl)-morpholine (11.28 g., 33.8 mmol) was dissolved in dioxane (100 mL) and to the reaction was added anhydrous hydrazine (11 g., 340 mmol). The reaction was heated at reflux for four hours. The solvent was removed under reduced pressure, and the crude solid was dissolved in a mixture of dichloromethane (400 mL) and 10% potassium carbonate (40 mL). The organic layer was isolated, dried with sodium sulfate, and evaporated to yield crude S7, (2-benzyloxymethyl-6-morpholin-4-yl-pyrimidin-4-yl)-hydrazine.

S7, (2-benzyloxymethyl-6-morpholin-4-yl-pyrimidin-4-yl)-hydrazine (658 mg., 2 mmol) was dissolved in ethanol (4 mL), and to the reaction was added m-tolylaldehyde (240 mg., 2 mmol) and one drop of glacial acetic acid. The reaction was stirred at 70° C. for sixteen hours, and the solvent was evaporated. The crude oil was purified by column chromatography to give Compound 91, N-[2-(2-benzyloxy-ethyl)-6-morpholin-4-yl-pyrimidin-4-yl]-N'-(3-methyl-benzylidene)-hydrazine (550 mg., 1.27 mmol.).

EXAMPLE 3

Synthesis of Compound 92

Compound 91, N-[2-(2-benzyloxy-ethyl)-6-morpholin-4-yl-pyrimidin-4-yl]-N'-(3-methyl-benzylidene)-hydrazine (109 mg., 0.25 mmol) was dissolved in ethanol (20 mL) and to the solution was added 10% palladium on carbon (200 mg.), three drops of glacial acetic acid, and the reaction was stirred at room temperature under 1 atmosphere of hydrogen for 4 hours. The reaction was passed through celite, evaporated and purified by column chromatography to give Compound 92, N-[2-(2-benzyloxy-ethyl)-6-morpholin-4-yl-pyrimidin-4-yl]-N'-(3-methyl-benzyl)-hydrazine (106 mg., 24 mmol).

EXAMPLE 4

Synthesis of Compound 12

Crude S7, (2-benzyloxymethyl-6-morpholin-4-yl-pyrimidin-4-yl)-hydrazine was dissolved in methanol (300 mL) and to the solution was added aqueous hydrochloric acid (6N, 80 mL) and 10% palladium on carbon (1 g.). The mixture was shaken in a Parr shaker under 59 psi of hydrogen. The reaction mixture was passed through celite and evaporated to give S8, 2-(4-hydrazino-6-morpholin-4-yl-pyrimidin-2-yl)-ethanol;

hydrochloride. The crude solid was dissolved in ethanol (50 mL). To the reaction mixture was added m-tolylaldehyde (4.1 g., 34 mmol) and ammonia in methanol (7N, 5 mL, 35 mmol). The reaction was stirred at 60° C. for 16 hours, and the solvent was evaporated. The reaction mixture was purified by column chromatography to give Compound 93, 2-{4-[N'-(3-methyl-benzylidene)-hydrazino]-6-morpholin-4-yl-pyrimidin-2-yl}-ethanol (2.0 g., 5.9 mmol).

Compound 12 was prepared in an analogous fashion to the last step in the preparation of Compound 1 except that Compound 93 was reacted with m-trifluoromethylphenylisocyanate.

Compound 15 was prepared in an analogous fashion to Compound 12 except that the isocyanate used was p-nitrophenylisocyanate.

Compound 17 was prepared in an analogous fashion to Compound 12 except that the isocyanate used was ethylisocyanate.

Compound 20 was prepared in an analogous fashion to Compound 12 except that the isocyanate used was p-isopropylphenylisocyanate.

Compound 21 was prepared in an analogous fashion to Compound 12 except that the isocyanate used was p-chlorophenylisocyanate.

Compound 22 was prepared in an analogous fashion to Compound 12 except that the isocyanate used was p-cyanophenylisocyanate as described above.

Compound 23 was prepared in an analogous fashion to Compound 12 except that the isocyanate used was p-isocyanato-benzoic acid methyl ester.

Compound 24 was prepared in an analogous fashion to Compound 12 except that the isocyanate used was phenylisocyanate.

EXAMPLE 5

Synthesis of Compound 94

Compound 93, 2-{4-[N'-(3-methyl-benzylidene)-hydrazino]-6-morpholin-4-yl-pyrimidin-2-yl}-ethanol (680 mg., 2 mmol) was dissolved in methylene chloride (10 mL) and to the reaction mixture was added diisopropylethylamine (0.6 mL, 3 mmol). The reaction was chilled to 0° C. To the reaction was added methanesulfonyl chloride (251 mg., 2.2 mmol). After fifteen minutes, the reaction was washed with saturated aqueous ammonium chloride (2×2 mL), dried with sodium sulfate, and purified by column chromatography to give Compound 95, methanesulfonic acid 2-{4-[N'-(3-methyl-benzylidene)-hydrazino]-6-morpholin-4-yl-pyrimidin-2-yl}-ethyl ester (290 mg., 0.7 mmol).

Compound 95, methanesulfonic acid 2-{4-[N'-(3-methyl-benzylidene)-hydrazino]-6-morpholin-4-yl-pyrimidin-2-yl}-ethyl ester (104 mg., 0.25 mmol) was dissolved in tetrahydrofuran (4 mL). To the reaction mixture was added morpholine (43 mg., 0.5 mmol) and the vessel was sealed and heated at 80° C. for sixteen hours. The solvent was removed under reduced pressure and the crude oil was purified by column chromatography to give Compound 94, N-(3-methyl-benzylidene)-N'-[6-morpholin-4-yl-2-(2-morpholin-4-yl-ethyl)-pyrimidin-4-yl]-hydrazine (52 mg., 0.13 mmol).

Compound 96 was prepared in an analogous fashion to Compound 94 as described above.

EXAMPLE 6

Synthesis of Compound 16

S9, 1-(4-chloro-6-morpholin-4-yl-pyrimidin-2-yl)-2-methyl-propan-2-ol, was prepared in an analogous fashion to S3 with acetone being used as the electrophile.

S10, 1-(4-hydrazino-6-morpholin-4-yl-pyrimidin-2-yl)-2-methyl-propan-2-ol, was prepared in an analogous fashion to S4 except that S9 was used instead of S3.

Compound 97, 2-methyl-1-{4-[N'-(3-methyl-benzylidene)-hydrazino]-6-morpholin-4-yl-pyrimidin-2-yl}-propan-2-ol, was prepared in an analogous fashion to S5 except that S10 was used instead of S4.

Compound 16 was prepared in an analogous fashion to Compound 12 as described above, using Compound 97 as the starting material and p-methylphenyl isocyanate. In addition, oxetane was used instead of oxirane.

Compound 98, 2-methyl-4-{4-[N'-(3-methyl-benzylidene)-hydrazino]-6-morpholin-4-yl-pyrimidin-2-yl}-butan-2-ol was prepared in an analogous fashion to Compound 97 as described above except that 1,1-dimethyl oxirane was used instead of oxirane.

Compound 29 was prepared in an analogous fashion to Compound 16 as described above except that the isocyanate used was m-trifluoromethylphenylisocyante.

Compound 30 was prepared in an analogous fashion to Compound 16 as described above except that the isocyanate used was p-trifluoromethylphenylisocyanate.

Compound 26 was prepared in an analogous fashion to Compound 16 as described above, using Compound 98 as the starting material and m-methylphenyl isocyanate was used as the isocyanate.

Compound 27 was prepared in an analogous fashion to Compound 26 as described above except that the isocyanate used was m-trifluoromethylphenylisocyanate.

Compound 28 was prepared in an analogous fashion to Compound 26 as described above, using Compound 99, 3-(4-Chloro-6-morpholin-4-yl-pyrimidin-2-yloxy)-2-methyl-propan-1-ol, as the starting material. Compound 99 was prepared in analogous fashion to the synthesis of 2-N-butoxy-4-chloro-6-(morpholin-4-yl) pyrimidine described in U.S. Pat. No. 6,693,097, the entire teachings of which are incorporated herein by reference, except that 2-methyl-hydroxypropanol was used as the alcohol.

EXAMPLE 7

Synthesis of Compound 100

Compound 101, 2-{4-[N'-(3-methyl-benzylidene)-hydrazino]-6-morpholin-4-yl-pyrimidin-2-yl}-ethylamine, was prepared in an analogous fashion to Compound 94 using ammonia as the nucleophile instead of morpholine.

Compound 101, 2-{4-[N'-(3-methyl-benzylidene)-hydrazino]-6-morpholin-4-yl-pyrimidin-2-yl}-ethylamine (40 mg., 0.2 mmol) was dissolved in dichloromethane (4 mL). To the reaction mixture was added diisopropylethylamine (129 mg., 1 mmol) and acetic anhydride (61 mg., 0.6 mmol) and the reaction was stirred at room temperature for one hour. The solvent was evaporated, and the organic layer was washed with saturated ammonium chloride (1 mL). The crude solid was purified by column chromatography to give Compound 100, N-(2-{4-[N-Acetyl-N'-(3-methyl-benzylidene)-hydrazino]-6-morpholin-4-yl-pyrimidin-2-yl}-ethyl)-acetamide (5 mg.)

EXAMPLE 8

Synthesis of Compound 25

Compound 95, methanesulfonic acid 2-{4-[N'-(3-methyl-benzylidene)-hydrazino]-6-morpholin-4-yl-pyrimidin-2-yl}-ethyl ester (50 mg., 0.12 mmol) was dissolved in tetrahydrofuran (2 mL). To the reaction mixture was added 5-pyridin-4-yl-4H-[1,2,4]triazole-3-thiol (124 mg., 0.66 mmol) and sodium hydride (12 mg., 0.5 mmol) and the vessel was stirred at room temperature for sixteen hours. The solvent was removed under reduced pressure and the crude oil was purified by column chromatography to give Compound 25, N-(3-methyl-benzylidene)-N'-{6-morpholin-4-yl-2-[2-(5-pyridin-4-yl-4H-[1,2,4]triazol-3-ylsulfanyl)-ethyl]-pyrimidin-4-yl}-hydrazine (34 mg.).

Compound 18 was prepared in an analogous fashion to Compound 25 as described above except that 1-(2-dimethylamino-ethyl)-1H-tetrazole-5-thiol was used instead of 5-pyridin-4-yl-4H-[1,2,4]triazole-3-thiol.

Example 9. Synthesis of Compound 102

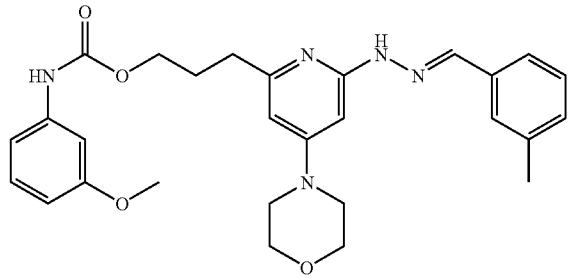

2-Methyl-4,6-dichloropyridine (256 mmol) is dissolved in dichloromethane (200 mL) and chilled to −78° C. in an inert atmosphere. Morpholine (550 mol) dissolved in dichloromethane (100 mL) is added slowly. The reaction is allowed to warm to room temperature while stirring overnight. The organic layer is washed with saturated ammonium chloride (2×100 mL), dried with sodium sulfate, and evaporated to give 2-methyl-4-chloro-6-morpholino-pyridine.

2-Methyl-4-chloro-6-morpholino-pyridine (50 mmol) is dissolved in tetrahydrofuran (200 mL). The reaction is chilled to −78° C. under an inert atmosphere. A solution of n-butyllithium in hexanes (24 mL, 2.5M, 60 mmol) is added, and the reaction mixture is stirred for thirty minutes. A solution of oxirane dissolved in tetrahydrofuran (40 mL, 41.5M, 60 mmol) is added, and the reaction is allowed to warm to room temperature while stirring overnight. The solvent is removed under reduced pressure, and the crude material is dissolved in methylene chloride (200 mL) and washed with saturated ammonium chloride (2×50 mL), dried with sodium sulfate, and evaporated to dryness. The compound is purified by column chromatography to give 3-(4-chloro-6-morpholin-4-yl-pyrid-2-yl)-propan-1-ol.

3-(4-Chloro-6-morpholin-4-yl-pyrid-2-yl)-propan-1-ol (19.4 mmol) is dissolved in dioxane (30 mL). To the reaction mixture is added anhydrous hydrazine (10 mL, 300 mmol). The reaction is then heated at reflux for five hours. The solvent is removed under reduced pressure, and the crude solid is dissolved in a mixture of dichloromethane (800 mL) and 10% potassium carbonate (40 mL). The organic layer is isolated, dried with sodium sulfate, and evaporated to yield crude 3-(4-hydrazino-6-morpholin-4-yl-pyrid-2-yl)-propan-1-ol (4.3 g., 17 mmol).

3-(4-hydrazino-6-morpholin-4-yl-pyrid-2-yl)-propan-1-ol (4.3 g., 17 mmol) is dissolved in ethanol (40 mL). To the mixture is added m-tolylaldehyde (2.15 g., 18 mmol) and one drop of glacial acetic acid. The reaction is heated at 50° C. for one hour, and then cooled to room temperature. The precipitate is filtered, washed with ethanol (10 mL) and dried in vacuo to give 3-{4-[N'-(3-methyl-benzylidene)-hydrazino]-6-morpholin-4-yl-pyrid-2-yl}-propan-1-ol.

3-{4-[N'-(3-methyl-benzylidene)-hydrazino]-6-morpholin-4-yl-pyrid-2-yl}-propan-1-ol (1 mmol) is dissolved in acetonitrile (4 mL). To the mixture is added m-methoxyphenylisocyanate (149 mg., 1 mmol) and a catalytic amount of dimethylaminopyridine. The reaction is stirred at 60° C. for 16 hours. The reaction is then cooled to 4° C., and the precipitate is filtered, washed with acetonitrile (1 mL) and dried to give Compound 102, (3-methoxy-phenyl)-carbamic acid 3-{4-[N'-(3-methyl-benzylidene)-hydrazino]-6-morpholin-4-yl-pyrid-2-yl}-propyl ester.

EXAMPLE 10

Synthesis of Compound 54

Compound 101, 2-{4-[N'-(3-methyl-benzylidene)-hydrazino]-6-morpholin-4-yl-pyrimidin-2-yl}-ethylamine, was prepared in an analogous fashion to Compound 94 using ammonia as the nucleophile.

Compound 101 (96 mg.; 0.22 mmol) was dissolved in dichloromethane (10 mL) and diisopropylethylamine (30 mg). To the solution was added dimethylsulfamoyl chloride (32 mg.), and the reaction was stirred overnight. The reaction mixture was washed with saturated ammonium chloride (2×10 mL), evaporated, and purified by column chromatography to give Compound 54, 1,1-Dimethyl-3-(2-{4-[N'-(3-methyl-benzylidene)-hydrazino]-6-morpholin-4-yl-pyrimidin-2-yl}-ethyl)-sulfamide.

EXAMPLE 11

Synthesis of Compound 55

2-{4-[N'-(3-Methyl-benzylidene)-hydrazino]-6-morpholin-4-yl-pyrimidin-2-yloxy}-ethanol (79 mg.; 0.22 mmol) was dissolved in tetrahydrofuran (10 mL) and chilled to −78° C. To the solution was slowly added n-butyl lithium (0.10 mL of a 2.5M solution; 0.25 mmol). After stirring for an additional twenty minutes, morpholinocarbonyl chloride (40 mg.) was added, and the solution was allowed to warm to room temperature slowly overnight. The solvent was evaporated, and the solid was purified by column chromatography to give Compound 55.

Compound 85 was made in an analogous fashion to Compound 55 except that dimethylaminocarbonyl chloride was used instead of morpholinocarbonyl chloride.

Example 12. Synthesis of Compound 103

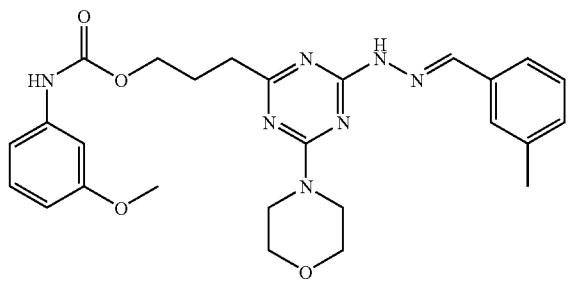

2-Methyl-4,6-dichlorotriazine (256 mmol) is dissolved in dichloromethane (200 mL) and chilled to −78° C. in an inert atmosphere. Morpholine (550 mol) dissolved in dichloromethane (100 mL) is added slowly. The reaction is allowed to warm to room temperature while stirring overnight. The organic layer is washed with saturated ammonium chloride (2×100 mL), dried with sodium sulfate, and evaporated to give 2-methyl-4-chloro-6-morpholino-triazine.

2-Methyl-4-chloro-6-morpholino-triazine (50 mmol) is dissolved in tetrahydrofuran (200 mL). The reaction is chilled to −78° C. under an inert atmosphere. A solution of n-butyl-lithium in hexanes (24 mL, 2.5M, 60 mmol) is added, and the reaction mixture is stirred for thirty minutes. A solution of oxirane dissolved in tetrahydrofuran (40 mL, 41.5M, 60 mmol) is added, and the reaction is allowed to warm to room temperature while stirring overnight. The solvent is removed under reduced pressure, and the crude material is dissolved in methylene chloride (200 mL) and washed with saturated ammonium chloride (2×50 mL), dried with sodium sulfate, and evaporated to dryness. The compound is purified by column chromatography to give 3-(4-chloro-6-morpholin-4-yl-triazin-2-yl)-propan-1-ol.

3-(4-Chloro-6-morpholin-4-yl-triazin-2-yl)-propan-1-ol (19.4 mmol) is dissolved in dioxane (30 mL). To the reaction mixture is added anhydrous hydrazine (10 mL, 300 mmol). The reaction is then heated at reflux for five hours. The solvent is removed under reduced pressure, and the crude solid is dissolved in a mixture of dichloromethane (800 mL) and 10% potassium carbonate (40 mL). The organic layer is isolated, dried with sodium sulfate, and evaporated to yield crude 3-(4-hydrazino-6-morpholin-4-yl-triazin-2-yl)-propan-1-ol (4.3 g., 17 mmol).

3-(4-hydrazino-6-morpholin-4-yl-triazin-2-yl)-propan-1-ol (4.3 g., 17 mmol) is dissolved in ethanol (40 mL). To the mixture is added m-tolylaldehyde (2.15 g., 18 mmol) and one drop of glacial acetic acid. The reaction is heated at 50° C. for one hour, and then cooled to room temperature. The precipitate is filtered, washed with ethanol (10 mL) and dried in vacuo to give 3-{4-[N'-(3-methyl-benzylidene)-hydrazino]-6-morpholin-4-yl-triazin-2-yl}-propan-1-ol.

3-{4-[N'-(3-methyl-benzylidene)-hydrazino]-6-morpholin-4-yl-triazin-2-yl}-propan-1-ol (1 mmol) is dissolved in acetonitrile (4 mL). To the mixture is added m-methoxyphenylisocyanate (149 mg., 1 mmol) and a catalytic amount of dimethylaminopyridine. The reaction is stirred at 60° C. for 16 hours. The reaction is then cooled to 4° C., and the precipitate is filtered, washed with acetonitrile (1 mL) and dried to give Compound 103, (3-methoxy-phenyl)-carbamic acid 3-{4-[N'-(3-methyl-benzylidene)-hydrazino]-6-morpholin-4-yl-triazin-2-yl}-propyl ester.

EXAMPLE 13

ESMS of Synthesized Compounds

The ESMS was calculated and measured for each of the compounds synthesized.

TABLE 1

| COMPOUND | CMPD NO. | CALCULATED ESMS | MEASURED ESMS (M + 1) |
|---|---|---|---|
| (3-Methoxy-phenyl)-carbamic acid 3-{4-[N'-(3-methyl-benzylidene)-hydrazino]-6-morpholin-4-yl-pyrimidin-2-yl}-propyl ester | 1 | 504.25 | 505.3 |
| (3-Trifluoromethyl-phenyl)-carbamic acid 3-{4-[N'-(3-methyl-benzylidene)-hydrazino]-6-morpholin-4-yl-pyrimidin-2-yl}-propyl ester | 2 | 542.23 | 543.2 |
| p-Tolyl-carbamic acid 3-{4-[N'-(3-methyl-benzylidene)-hydrazino]-6-morpholin-4-yl-pyrimidin-2-yl}-propyl ester | 3 | 488.25 | 489.3 |
| (3-Trifluoromethyl-phenyl)-carbamic acid 3-{4-[N-methyl-N'-(3-methyl-benzylidene)-hydrazino]-6-morpholin-4-yl-pyrimidin-2-yl}-propyl ester | 4 | 556.24 | 557.3 |
| Cyclohexyl-carbamic acid 3-{4-[N'-(3-methyl-benzylidene)-hydrazino]-6-morpholin-4-yl-pyrimidin-2-yl}-propyl ester | 5 | 480.28 | 481.3 |
| (2-Fluoro-phenyl)-carbamic acid 3-{4-[N'-(3-methyl-benzylidene)-hydrazino]-6-morpholin-4-yl-pyrimidin-2-yl}-propyl ester | 6 | 492.23 | 493.2 |
| (4-Nitro-phenyl)-carbamic acid 3-{4-[N'-(3-methyl-benzylidene)-hydrazino]-6-morpholin-4-yl-pyrimidin-2-yl}-propyl ester | 7 | 519.22 | 520.2 |

TABLE 1-continued

| COMPOUND | CMPD NO. | CALCULATED ESMS | MEASURED ESMS (M + 1) |
|---|---|---|---|
| Ethyl-carbamic acid 3-{4-[N'-(3-methyl-benzylidene)-hydrazino]-6-morpholin-4-yl-pyrimidin-2-yl}-propyl ester | 8 | 426.24 | 427.2 |
| Pyridin-3-yl-thiocarbamic acid O-(3-{4-[N'-(3-methyl-benzylidene)-hydrazino]-6-morpholin-4-yl-pyrimidin-2-yl}-propyl) ester | 9 | 491.21 | 492.2 |
| Naphthalen-1-yl-carbamic acid 3-{4-[N'-(3-methyl-benzylidene)-hydrazino]-6-morpholin-4-yl-pyrimidin-2-yl}-propyl ester | 10 | 524.25 | 525.3 |
| (4-Phenoxy-phenyl)-carbamic acid 3-{4-[N'-(3-methyl-benzylidene)-hydrazino]-6-morpholin-4-yl-pyrimidin-2-yl}-propyl ester | 11 | 566.26 | 567.3 |
| (3-Trifluoromethyl-phenyl)-carbamic acid 2-{4-[N'-(3-methyl-benzylidene)-hydrazino]-6-morpholin-4-yl-pyrimidin-2-yl}-ethyl ester | 12 | 528.21 | 529.2 |
| p-Tolyl-carbamic acid 2-{4-[N'-(3-methyl-benzylidene)-hydrazino]-6-morpholin-4-yl-pyrimidin-2-yl}-ethyl ester | 13 | 474.24 | 475.2 |
| p-Tolyl-carbamic acid 3-{4-[N-methyl-N'-(3-methyl-benzylidene)-hydrazino]-6-morpholin-4-yl-pyrimidin-2-yl}-propyl ester | 14 | 502.27 | 503.3 |
| (4-Nitro-phenyl)-carbamic acid 2-{4-[N'-(3-methyl-benzylidene)-hydrazino]-6-morpholin-4-yl-pyrimidin-2-yl}-ethyl ester | 15 | 505.21 | 506.2 |
| p-Tolyl-carbamic acid 1,1-dimethyl-2-{4-[N'-(3-methyl-benzylidene)-hydrazino]-6-morpholin-4-yl-pyrimidin-2-yl}-ethyl ester | 16 | 502.27 | 503.3 |
| Ethyl-carbamic acid 2-{4-[N'-(3-methyl-benzylidene)-hydrazino]-6-morpholin-4-yl-pyrimidin-2-yl}-ethyl ester | 17 | 412.22 | 413.2 |
| Dimethyl-{2-[5-(2-{4-[N'-(3-methyl-benzylidene)-hydrazino]-6-morpholin-4-yl-pyrimidin-2-yl}-ethylsulfanyl)-tetrazol-1-yl]-ethyl}-amine | 18 | 496.25 | 497.2 |
| p-Tolyl-carbamic acid 2-{4-[N'-(3-methyl-benzylidene)-hydrazino]-6-morpholin-4-yl-pyrimidin-2-yloxy}-ethyl ester | 19 | 490.23 | 491.2 |
| (4-Isopropyl-phenyl)-carbamic acid 2-{4-[N'-(3-methyl-benzylidene)-hydrazino]-6-morpholin-4-yl-pyrimidin-2-yl}-ethyl ester | 20 | 502.27 | 503.3 |
| (4-Chloro-phenyl)-carbamic acid 2-{4-[N'-(3-methyl-benzylidene)-hydrazino]-6-morpholin-4-yl-pyrimidin-2-yl}-ethyl ester | 21 | 494.18 | 495.2 |
| (4-Cyano-phenyl)-carbamic acid 2-{4-[N'-(3-methyl-benzylidene)-hydrazino]-6-morpholin-4-yl-pyrimidin-2-yl}-ethyl ester | 22 | 485.22 | 486.2 |
| 4-(2-{4-[N'-(3-Methyl-benzylidene)-hydrazino]-6-morpholin-4-yl-pyrimidin-2-yl}-ethoxycarbonylamino)-benzoic acid methyl ester | 23 | 518.23 | 486.2 |
| Phenyl-carbamic acid 2-{4-[N'-(3-methyl-benzylidene)-hydrazino]-6-morpholin-4-yl-pyrimidin-2-yl}-ethyl ester | 24 | 460.22 | 461.2 |
| N-(3-Methyl-benzylidene)-N'-{6-morpholin-4-yl-2-[2-(5-pyridin-4-yl-4H-[1,2,4]triazol-3-ylsulfanyl)-ethyl]-pyrimidin-4-yl}-hydrazine | 25 | 501.21 | 502.2 |
| m-Tolyl-carbamic acid 1,1-dimethyl-3-{4-[N'-(3-methyl-benzylidene)-hydrazino]-6-morpholin-4-yl-pyrimidin-2-yl}-propyl ester | 26 | 516.28 | 517.3 |
| (3-Trifluoromethyl-phenyl)-carbamic acid 1,1-dimethyl-3-{4-[N'-(3-methyl- | 27 | 570.26 | 571.3 |

TABLE 1-continued

| COMPOUND | CMPD NO. | CALCULATED ESMS | MEASURED ESMS (M + 1) |
|---|---|---|---|
| benzylidene)-hydrazino]-6-morpholin-4-yl-pyrimidin-2-yl}-propyl ester | | | |
| (3-Trifluoromethyl-phenyl)-carbamic acid 1,1-dimethyl-2-{4-[N'-(3-methyl-benzylidene)-hydrazino]-6-morpholin-4-yl-pyrimidin-2-yloxy}-ethyl ester | 28 | 572.24 | 573.3 |
| (3-Trifluoromethyl-phenyl)-carbamic acid 1,1-dimethyl-2-{4-[N'-(3-methyl-benzylidene)-hydrazino]-6-morpholin-4-yl-pyrimidin-2-yl}-ethyl ester | 29 | 556.24 | 557.3 |
| (4-Trifluoromethyl-phenyl)-carbamic acid 1,1-dimethyl-2-{4-[N'-(3-methyl-benzylidene)-hydrazino]-6-morpholin-4-yl-pyrimidin-2-yl}-ethyl ester | 30 | 556.24 | 557.2 |
| 1,1-Dimethyl-3-(2-{4-[N'-(3-methyl-benzylidene)-hydrazino]-6-morpholin-4-yl-pyrimidin-2-yl}-ethyl)-sulfamide | 54 | 447.21 | 448.1 |
| Morpholine-4-carboxylic acid 2-{2-[N'-(3-methyl-benzylidene)-hydrazino]-6-morpholin-4-yl-pyrimidin-4-yloxy}-ethyl ester | 55 | 470.23 | 471.2 |
| Dimethyl-carbamic acid 2-{2-[N'-(3-methyl-benzylidene)-hydrazino]-6-morpholin-4-yl-pyrimidin-4-yloxy}-ethyl ester | 85 | 428.22 | 429.2 |
| Propyl-carbamic acid 2-{2-[N'-(3-methyl-benzylidene)-hydrazino]-6-morpholin-4-yl-pyrimidin-4-yloxy}-ethyl ester | 104 | 442.23 | 443.2 |
| (4-Methoxy-benzyl)-carbamic acid 2-{2-[N'-(3-methyl-benzylidene)-hydrazino]-6-morpholin-4-yl-pyrimidin-4-yloxy}-ethyl ester | 105 | 520.24 | 521.2 |
| Pyridin-3-yl-carbamic acid 2-{4-[N'-(3-methyl-benzylidene)-hydrazino]-6-morpholin-4-yl-pyrimidin-2-yloxy}-ethyl ester | 106 | 477.21 | 478.1 |

EXAMPLE 14

In Vitro Assays

Reagents. *Staphylococcus aureus* Cowan I (SAC) was obtained from Calbiochem (La Jolla, Calif.), and lipopolysaccharide (LPS, *Serratia marscencens*) was obtained from Sigma (St. Louis, Mo.). Human and mouse recombinant IFNγ were purchased from Boehringer Mannheim (Mannheim, Germany) and Pharmingen (San Diego, Calif.), respectively.

Human In Vitro Assay. Human PBMC were isolated by centrifugation using Ficoll-Paque (Pharmacia Biotech, Uppsala, Sweden) and prepared in RPMI medium supplemented with 10% fetal calf serum (FCS), 100 U/mL penicillin, and 100 μg/mL streptomycin. PBMC were plated in wells of a 96-well plate at a concentration of $5 \times 10^5$ cells/well, and primed by adding IFNγ (30 U/mL) for 22 h and stimulated by adding LPS (1 μg/mL), or by adding IFNγ (100 U/mL) and then stimulated by adding SAC (0.01%). A test pyrimidine compound was dissolved in DMSO, and added to wells of the 96-well plate. The final DMSO concentration was adjusted to 0.25% in all cultures, including the compound-free control. Human THP-1 cells were plated in wells, primed by adding IFNγ (100 U/mL) for 22 h and stimulated by adding SAC (0.025%) in the presence of different concentrations of the pyrimidine compound. Cell-free supernatants were taken 18 h later for measurement of cytokines. Cell viability was assessed using the bioreduction of MTS. Cell survival was estimated by determining the ratio of the absorbance in compound-treated groups versus compound-free control.

The supernatant was assayed for the amount of IL-12p40, IL-12p70, or IL-10 by using a sandwich ELISA with anti-human antibodies, i.e., a Human IL-12 p40 ELISA kit from R&D Systems (Berkeley, Calif.), and a Human IL-12 p70 or IL-10 ELISA kit from Endogen (Cambridge, Mass.). Assays were based on the manufacturer's instructions.

Murine In Vitro Assay. Balb/c mice (Taconic, Germantown, N.Y.) were immunized with *Mycobacterium tuberculosis* H37Ra (Difco, Detroit, Mich.). The splenocytes were harvested 5 days and prepared in RPMI medium supplemented with 10% FCS and antibiotics in a flat bottom 96-well plate with $1 \times 10^6$ cells/well. The splenocytes were then stimulated with a combination of IFNγ (60 ng/mL) and SAC (0.025%) [or LPS (20 μg/mL)] in the presence of a test compound. Cell-free supernatants were taken 24 h later for the measurement of cytokines. The preparation of compound and the assessment of cell viability were carried out as described above. Mouse IL-12 p70, IL-10, IL-1β, and TNFα were measured using ELISA kits from Endogen, according to the manufacturer's instructions.

The biological activities of pyrimidine compounds were tested on human PBMC or THP-1 cells. Unexpectedly, some of the test compounds have $IC_{50}$ values as low as <1 nM. Representative results are shown in Table 2.

TABLE 2

Representative in vitro IC50 data
(A = <25 nM; B = 25–50 nM; C = >50 nM)

| Compound | IC50 (nM) |
| --- | --- |
| 1 | B |
| 2 | A |
| 3 | A |
| 4 | C |
| 5 | A |
| 6 | A |
| 7 | A |
| 8 | A |
| 9 | A |
| 10 | C |
| 11 | B |
| 12 | A |
| 13 | A |
| 14 | A |
| 15 | A |
| 16 | A |
| 17 | A |
| 18 | A |
| 19 | A |
| 20 | C |
| 21 | B |
| 22 | A |
| 23 | A |
| 24 | A |
| 25 | A |
| 26 | B |
| 27 | C |
| 28 | A |
| 29 | C |
| 30 | A |
| 54 | A |
| 55 | A |
| 85 | A |
| 104 | A |
| 105 | A |
| 106 | A |

EXAMPLE 15

In Vivo Assays

Treatment of adjuvant arthritis in rats: Adjuvant arthritis (AA) was induced in female Lewis rats by the intracutaneous injection (base of the tail) of 0.1 mL of a 10 mg/mL bacterial suspension made from ground, heat-killed *Mycobacterium tuberculosis* H37Ra suspended in incomplete Freund's adjuvant. Rats were given a test compound orally once a day for 12 days, starting the day following the induction. The development of polyarthritis was monitored daily by macroscopic inspection and assignment of an arthritis index to each animal, during the critical period (days 10 to 25 post-immunization).

The intensity of polyarthritis was scored according to the following scheme: (a) Grade each paw from 0 to 3 based on erythema, swelling, and deformity of the joints: 0 for no erythema or swelling; 0.5 if swelling is detectable in at least one joint; 1 for mild swelling and erythema; 2 for swelling and erythema of both tarsus and carpus; and 3 for ankylosis and bony deformity. Maximum score for all 4 paws was thus 12. (b) Grade for other parts of the body: for each ear, 0.5 for redness and another 0.5 if knots are present; 1 for connective tissue swelling (saddle nose); and 1 for the presence of knots or kinks in the tail. The highest possible arthritic index was 16.

Oral administration of pyrimidine compounds of this invention (e.g., Compound 12) reproducibly reduced the arthritic score and delayed the development of polyarthritis in a dose-dependent manner. The arthritis score used in this model was a reflection of the inflammatory state of the structures monitored and the results therefore show the ability of the test compound to provide relief for this aspect of the pathology.

Treatment of Crohn's disease in dinitrobenzene sulfonic acid-induced inflammatory bowel syndrome model rats: Wistar derived male or female rats weighing 200±20 g and fasted for 24 hours were used. Distal colitis was induced by intra-colonic instillation of 2,4-dinitrobenzene sulfonic acid (DNBS, 25 mg in 0.5 mL ethanol 30%) after which air (2 mL) was gently injected through the cannula to ensure that the solution remained in the colon. A test compound and/or vehicle was administered orally 24 and 2 hours before DNBS instillation and then daily for 5 days. One control group was similarly treated with vehicle alone while the other is treated with vehicle plus DNBS. The animals were sacrificed 24 hours after the final dose of test compound administration and each colon was removed and weighed. Colon-to-body weight ratio was then calculated for each animal according to the formula: Colon (g)/BW×100. The "Net" increase in ratio of Vehicle-control+DNBS group relative to Vehicle-control group was used as a base for comparison with test substance treated groups and expressed as "% Deduction." Pyrimidine compounds of this invention (e.g., Compound 12) reproducibly had about 30% deduction. A 30% or more reduction in colon-to-body weight ratio, relative to the vehicle treated control group, was considered significant.

Rats treated with test substance orally showed a marked reduction in the inflammatory response. These experiments were repeated three times and the effects were reproducible.

Treatment of Crohn's disease in $CD4^+$ $CD45Rb^{high}$ T cell-reconstituted SCID colitis model mice: Spleen cells were prepared from normal female BALB/c mice. For cell purification, the following anti-mouse antibodies were used to label non-$CD4^+$ T cells: B220 (RA3-6B2), CD11b (M1/70), and $CD8\alpha$ (53-6.72). All antibodies were obtained from BioSource (Camarillo, Calif.). M450 anti-rat IgG-coated magnetic beads (Dynal, Oslo, Norway) were used to bind the antibodies and negative selection was accomplished using an MPC-1 magnetic concentrator. The enriched $CD4^+$ cells were then labeled for cell sorting with FITC-conjugated CD45RB (16A, Pharmingen, San Diego, Calif.) and PE-conjugated CD4 (CT-CD4, Caltag, Burlingame, Calif.). $CD4^+$ $CD45RB^{high}$ cells were operationally defined as the upper 40% of CD45Rb-staining $CD4^+$ cells and sorted under sterile conditions by flow cytometry. Harvested cells were resuspended at $4\times10^6$/mL in PBS and injected 100 µL intraperitoneally into female C.B-17 SCID mice. Pyrimidine compounds of this invention (e.g., Compound 12) and/or vehicle was orally administered once a day, 5 days per week, starting the day following the transfer. The transplanted SCID mice were weighed weekly and their clinical condition was monitored.

Colon tissue samples were fixed in 10% buffered formalin and embedded in paraffin. Sections (4 µm) collected from ascending, transverse, and descending colon were cut and stained with hematoxylin and eosin. The severity of colitis was determined based on histological examination of the distal colon sections, whereby the extent of colonic inflammation was graded on a scale of 0-3 in each of four criteria: crypt elongation, cell infiltration, depletion of goblet cells, and the number of crypt abscesses.

LP lymphocytes were isolated from freshly obtained colonic specimens. After removal of payer's patches, the colon was washed in Ca/Mg-free HBSS, cut into 0.5 cm pieces and incubated twice in HBSS containing EDTA (0.75 mM), DTT (1 mM), and antibiotics (amphotericin 2.5 µg/mL, gentamicin 50 µg/mL from Sigma) at 37° C. for 15 min. Next, the tissue was digested further in RPMI containing 0.5 mg/mL collagenase D, 0.01 mg/mL DNase I (Boehringer Manheim), and antibiotics at 37° C. LP cells were then layered on a 40-100% Percoll gradient (Pharmacia, Uppsala, Sweden), and lymphocyte-enriched populations were isolated from the cells at the 40-100% interface.

To measure cytokine production, 48-well plates were coated with 10 µg/mL murine anti-CD3ε antibody (145-2C11) in carbonate buffer (PH 9.6) overnight at 4° C. $5 \times 10^5$ LP cells were then cultured in 0.5 ml of complete medium in precoated wells in the presence of 1 µg/mL soluble anti-CD28 antibody (37.51). Purified antibodies were obtained from Pharmingen. Culture supernatants were removed after 48 h and assayed for cytokine production. Murine IFNγ was measured using an ELISA kit from Endogen (Cambridge, Mass.), according to the manufacturer's instructions.

Histological analysis showed that oral administration of pyrimidine compounds of this invention (e.g., Compound 12) reduced colonic inflammation as compared to vehicle control. The suppressive effect was dose-dependent with a substantial reduction at a dose of 10 mg/kg. The calculated colon-to-body weight ratio was consistent with the histological score, showing attenuation by treatment with the test compound. Furthermore, analysis of cytokines from LP cells in response to anti-CD3 antibody and anti-CD28 antibody demonstrated that LP cells from vehicle control produced an augmented level of IFNγ and treatment with test substance greatly diminished the production. These results clearly demonstrated the potential of the test substance in treatment of inflammatory bowel disease represented by Crohn's disease.

The contents of all patents, patent applications, and publications cited throughout this specification are hereby incorporated herein by reference in their entirety.

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. For example, compounds structurally analogous to a heterocyclic compound described in the specification also can be made, screened for their inhibiting IL-12 activities, and used to practice this invention. Thus, other embodiments are also within the claims.

What is claimed is:

1. A compound of formula (I) or a pharmaceutically acceptable salt thereof:

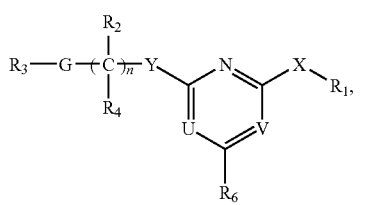

(I)

wherein
$R_1$ is

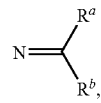

—N($R^c$)(CH$_2$)$_n$$R^c$; cycloalkyl, aryl, or heteroaryl;

for each occurrence, each of $R_2$ and $R_4$, independently, is $R^c$, halogen, nitro, cyano, isothionitro, S$R^c$, or O$R^c$; or $R_2$ and $R_4$, taken together, is carbonyl, $R_3$ is $R^c$, alkenyl, alkynyl, O$R^c$, OC(O)$R^c$, SO$_2$$R^c$, S(O)$R^c$, S(O$_2$)N$R^c$$R^d$, S$R^c$, N$R^c$$R^d$, N$R^c$CO$R^d$, N$R^c$C(O)O$R^d$, N$R^c$C(O)N$R^c$$R^d$, N$R^c$SO$_2$$R^d$, C(O)$R^c$, C(O)$R^c$, C(O)O$R^c$, or C(O)N$R^c$$R^d$; P(O)OR$^c$O$R^d$; S(O)$_2$N$R^c$$R^d$;

$R_5$ is H or alkyl;

$R_6$ is

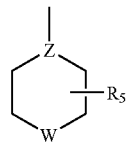

Each n is independently 0, 1, 2, 3, 4, 5, or 6;
G is:
Hydrazide;
Hydrazone;
Hydrazine;
Hydroxylamine;
Oxime;
Carbamate;
Thiocarbamate;
Guanidine;
Alkylguanidine;
—N$R^c$—C(N$R^c$)—NH—;
Cyanoguanidine;
Sulfonylguanidine;
—N$R^c$—C(NSO$_2$$R^d$)—NH—;
Nitroguanidine;
Acylguanidine;
Urea;
—N$R^c$—C(O)—N$R^c$—;
Thiourea;
—N$R^c$—C(S)—N$R^c$—;
—NH—S(O)$_2$—NH—;
—N$R^c$—S(O)$_2$—N$R^c$—;
Sulfonamide;
Phosphoryl;
-Heteroaryl-S—;
—C(N—CN)—N$R^c$—;
—Si(OH)$_2$—;
—B(OH)—
—C(N$R^d$)—N$R^c$—;
—N($R^c$)—CH$R^d$—C(O)—;
—C(O)—ON ($R^c$)—;
—C(O)—N($R^c$)O—;
—C(S)—ON($R^c$)—;
—C(S)—N($R^c$)O—;
—C(N($R^d$))—ON($R^c$)—;
—C(N($R^d$))—N$R^c$O—;
—OS(O)$_2$—N($R^c$)N($R^c$)—;

—OC(O)—N(R$^c$)N(R$^c$)—;
—OC(S)—N(R$^c$)N(R$^c$)—;
—OC(N(R$^d$))—N(R$^c$)N(R$^c$)—;
—N(R$^c$)N(R$^c$)S(O)$_2$O—;
—N(R$^c$)N(R$^c$)C(S)O—;
—N(R$^c$)N(R$^c$)C(N(R$^d$))O—;
—OP(O)$_2$O—;
—N(R$^c$)P(O)$_2$O—;
—OP(O)$_2$N(R$^c$)—;
—N(R$^c$)P(O)$_2$N(R$^c$)—;
—P(O)$_2$O—;
—P(O)$_2$N(R$^c$)—;
—N(R$^c$)P(O)$_2$—;
—OP(O)$_2$—;
—O-alkyl-heterocyclyl-N(R$^c$)—;
—N(R$^c$)CHR$^d$C(O)N(R$^c$)CHR$^d$C(O)—;
—N(R$^c$)CHR$^d$C(O)—;
—N(R$^c$)C(O)CHR$^d$—; or
—C(O)N(R$^c$)CHR$^d$C(O)—;
X is O, S, S(O), S(O$_2$), N(SO$_2$R$^c$), or NR$^c$;
Y is a covalent bond, CH$_2$, C(O), C=N—R$^c$, C=N—OR$^c$, C=N—SR$^c$, O, S, S(O), S(O$_2$), or NR$^c$;
Z is N or CH;
U is N and V is CR$^c$; and
W is O, S, S(O), S(O$_2$), NR$^c$, or NC(O)R$^c$;
wherein each of R$^a$ and R$^b$, independently, is H, alkyl, aryl, heteroaryl; and each of R$^c$, and R$^d$, independently, is H, alkyl, aryl, heteroaryl, cyclyl, heterocyclyl, —S(O)$_2$R$^d$, or alkylcarbonyl.

2. The compound of claim 1, wherein G is —C(O)NHNH—, —NHNHC(O)—, —C(O)NR$^f$NR$^g$—, —NR$^f$N-R$^g$C(O)—, —CH=N—NH—, —NH—N=CH—CR$^g$=N—NR$^f$—, —NR$^f$—N=CR$^g$—, —NHNH—, —NR$^f$NR$^g$—, —NHO— —O—NH—, —O—NR$^c$—, —NR$^c$—O—, —CH=N—O—, —O—N=CH—, —CR$^f$=N—O—, —O—N=CR$^f$—, —O—C(O)—NH—, —O—C(O)—NR$^f$—, —O—C(S)—NH—, —NH—C(S)—O—, —O—C(S)—NR$^f$—, —NR$^c$C(S)—O—, —NH—C(NH)—NH—, —NR$^c$—C(NH)—NH—, —NR$^c$—C(NR$^c$)—NH—, —NH—C(N(CN))—NH—, —NH—C(NSO$_2$R$^c$)—NH—, —NR$^c$—C(NSO$_2$R$^d$)—NH—, —NH—C(NNO$_2$)—NH—, —NH—C(NC(O)R$^c$)—NH—, —NH—C(O)—NH—, —NR$^c$—C(O)—NR$^c$—, —NH—C(S)—NH—, —NR$^c$—C(S)—NR$^c$—, —NH—S(O)$_2$—NH—, —NR$^c$—S(O)$_2$—NR$^c$—, —N(R$^c$)—S(O)$_2$—O—, —P(O)(R$^c$)—, —P(O)(R$^c$)—O—, —P(O)(R$^c$)—NR$^c$—, -Heteroaryl-S—, —C(N—CN)—NH—, —Si(OH)$_2$—, —B(OH)—, —C(NH)—NR$^c$—, —N(R$^c$)—CH$_2$—C(O)—, —C(O)—ON(R$^c$)—, —C(O)—N(R$^c$)O—, —C(S)—ON(R$^c$)—, —C(S)—N(R$^c$)O—, —C(N(R$^d$))—ON(R$^c$)—, —C(N(R$^d$))—NR$^c$O—, —OS(O)$_2$—N(R$^c$)N(R$^c$)—, —OC(O)—N(R$^c$)N(R$^c$)—, —OC(S)—N(R$^c$)N(R$^c$)—, —OC(N(R$^d$))—N(R$^c$)N(R$^c$)—, —N(R$^c$)N(R$^c$)S(O)$_2$O—, —N(R$^c$)N(R$^c$)C(S)O—, —N(R$^c$)N(R$^c$)C(N(R$^d$))O—, —OP(O)$_2$O—, —N(R$^c$)P(O)$_2$O—, —OP(O)$_2$N(R$^c$)—, —N(R$^c$)P(O)$_2$N(R$^c$)—, —P(O)$_2$O—, —P(O)$_2$N(R$^c$), —N(R$^c$)P(O)$_2$—, —OP(O)$_2$—, —O-alkyl-heterocyclyl-N(R$^c$)—, —N(R$^c$)CHR$^d$C(O)N(R$^c$)CHR$^d$C(O)—, —N(R$^c$)CHR$^d$C(O)—, —N(R$^c$)C(O)CHR$^d$—, and —C(O)N(R$^c$)CHR$^d$C(O)—;
wherein R$^f$, R$^g$ and R$^h$, for each occurrence is H, alkyl, aryl, heteroaryl, aralkyl, cycle, and heterocyclyl.

3. The compound of claim 1, wherein G is —C(O)NHNH—, —NHNHC(O)—, —CH=N—NH—, —NH—N=CH—, —NHNH—, —NHO—, —O—NH—, —NR$^c$—O—, —CH=N—O—, —O—N=CH—, —O—C(S)—NH—, or —NH—C(S)—O—.

4. The compound of claim 1, wherein G is —O—C(O)—NH—, —NH—C(NH)—NH—, —NR$^c$—C(NH)—NH—, —NR$^c$—C(NR$^c$)—NH—, —NH—C(N(CN))—NH—, —NH—C(NSO$_2$R$^c$)—NH, —NR$^c$—C(NSO$_2$R$^d$)—NH—, NH—C(NNO$_2$)—NH—, NH—C(NC(O)R)—NH—, —NH—C(O)—NH—, or —NH—C(S)—NH—.

5. The compound of claim 1, wherein G is —NH—S(O)$_2$—NH—, —N(R$^c$)—S(O)$_2$—O—, —P(O)(R$^c$)—, —P(O)(R$^c$)—O—, or —P(O)(R$^c$)—NR$^c$—.

6. The compound of claim 1, wherein G is —C(N—CN)—NH—, —Si(OH)$_2$—, —C(NH)—NR$^c$—, or —N(R$^c$)—CH$_2$—C(O)—.

7. The compound of claim 1, wherein X is NR$^c$.

8. The compound of claim 7, wherein R$^c$ in X is H, alkyl, or alkylcarbonyl.

9. The compound of claim 1, wherein X is O.

10. The compound of claim 1, wherein R$_1$ is

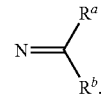

11. The compound of claim 10, wherein one of R$^a$ or R$^b$ is H.

12. The compound of claim 10, wherein one of R$^a$ or R$^b$ is alkyl.

13. The compound of claim 10, wherein one of R$^a$ or R$^b$ is aryl.

14. The compound of claim 10, wherein one of R$^a$ or R$^b$ is heteroaryl.

15. The compound of claim 1, wherein R$_1$ is aryl or heteroaryl.

16. The compound of claim 1, wherein R$^c$ in V is H.

17. The compound of claim 1, wherein U is CR$^c$ and V is N.

18. The compound of claim 17, wherein R$^c$ in U is H.

19. The compound of claim 1, wherein Z is N.

20. The compound of claim 1, wherein W is O.

21. The compound of claim 1, wherein R$_5$ is H.

22. The compound of claim 1, wherein Y is CH$_2$, O, or a covalent bond.

23. The compound of claim 1, wherein n is 0, 1, or 2.

24. The compound of claim 1, wherein each of R$_2$ and R$_4$ is R$^c$.

25. The compound of claim 24, wherein R$^c$ in R$_2$ and R$_4$ is H.

26. The compound of claim 24, wherein R$^c$ in R$_4$ is alkyl.

27. The compound of claim 1, wherein R$_3$ is R$^c$, COR$^c$, C(O)R$^c$, SO$_2$R$^c$, or S(O)$_2$NR$^c$R$^d$.

28. The compound of claim 27, wherein R$_3$ is R$^c$, and R$^c$ in R$_3$ is H, alkyl, aryl, cyclyl, or heterocyclyl.

29. The compound of claim 27, wherein R$_3$ is COR$^c$, and R$^c$ in R$_3$ is H.

30. The compound of claim 27, wherein R$_3$ is SO$_2$R$^c$, and R$^c$ in R$_3$ is cyclyl.

31. A compound of claim 1, wherein the compound is (3-Methoxy-phenyl)-carbamic acid 3-{4-[N'-(3-methyl-benzylidene)-hydrazino]-6-morpholin-4-yl-pyrimidin-2-yl}-propyl ester, (3-Trifluoromethyl-phenyl)-carbamic acid 3-{4-[N'-(3-methyl-benzylidene)-hydrazino]-6-morpholin-4-yl-pyrimidin-2-yl}-propyl ester, p-Tolyl-carbamic acid 3-{4-[N'-(3-methyl-benzylidene)-hydrazino]-6-morpholin-4-yl-pyrimidin-2-yl}-propyl ester, (3-Trifluoromethyl-phenyl)-carbamic acid 3-{4-[N-methyl-N'-(3-methyl-benzylidene)-hydrazino]-6-morpholin-4-yl-pyrimidin-2-yl}-propyl ester, Cyclohexyl-carbamic acid 3-{4-[N'-(3-methyl-benzylidene)-hydrazino]-6-morpholin-4-yl-pyrimidin-2-yl}-propyl ester, (2-Fluoro-phenyl)-carbamic acid 3-{4-[N'-(3-methyl-benzylidene)-hydrazino]-6-morpholin-4-yl-pyrimidin-2-yl}-propyl ester, (4-Nitro-phenyl)-carbamic acid 3-{4-[N'-(3-methyl-benzylidene)-hydrazino]-6-morpholin-4-yl-pyrimidin-2-yl}-propyl ester, Ethyl-carbamic acid 3-{4-[N'-(3-methyl-benzylidene)-hydrazino]-6-morpholin-4-yl -pyrimidin-2-yl}-propyl ester, Pyridin-3-yl-thiocarbamic acid O-(3-{4-[N'-(3-methyl -benzylidene)-hydrazino]-6-morpholin-4-yl-pyrimidin-2-yl}-propyl) ester, Naphthalen-1-yl-carbamic acid 3-{4-[N'-(3-methyl-benzylidene)-hydrazino]-6-morpholin-4-yl-pyrimidin-2-yl}-propyl ester, (4-Phenoxy-phenyl)-carbamic acid 3-{4-[N'-(3-methyl-benzylidene)-hydrazino]-6-morpholin-4-yl-pyrimidin-2-yl}-propyl ester, (3-Trifluoromethyl-phenyl)-carbamic acid 2-{4-[N'-(3-methyl-benzylidene)-hydrazino]-6-morpholin-4-yl-pyrimidin-2-yl}-ethyl ester, p-Tolyl-carbamic acid 2-{4-[N'-(3-methyl-benzylidene)-hydrazino]-6-morpholin-4-yl-pyrimidin-2-yl}-ethyl ester, p-Tolyl-carbamic acid 3-{4-[N-methyl-N'-(3-methyl-benzylidene)-hydrazino]-6-morpholin-4-yl-pyrimidin-2-yl}-propyl ester, (4-Nitro -phenyl)-carbamic acid 2-{4-[N'-(3-methyl-benzylidene)-hydrazino]-6-morpholin-4-yl -pyrimidin-2-yl}-ethyl ester, p-Tolyl-carbamic acid 1,1-dimethyl-2-{4-[N'-(3-methyl -benzylidene)-hydrazino]-6-morpholin-4-yl-pyrimidin-2-yl}-ethyl ester, Ethyl-carbamic acid 2-{4-[N'-(3-methyl-benzylidene)-hydrazino]-6-morpholin-4-yl-pyrimidin-2-yl}-ethyl ester, Dimethyl-{2-[5-(2-{4-[N'-(3-methyl benzylidene)-hydrazino]-6-morpholin-4-yl -pyrimidin-2-yl}-ethylsulfanyl)-tetrazol-1-yl]-ethyl}-amine, p-Tolyl-carbamic acid 2-{4-[N'-(3-methyl-benzylidene)-hydrazino]-6-morpholin-4-yl-pyrimidin-2-yloxy}-ethyl ester, (4-Isopropyl-phenyl)-carbamic acid 2-{4-[N'-(3-methyl-benzylidene)-hydrazino]-6-morpholin-4-yl-pyrimidin-2-yl}-ethyl ester, (4-Chloro-phenyl)-carbamic acid 2-{4-[N'-(3-methyl-benzylidene)-hydrazino]-6-morpholin-4-yl-pyrimidin-2-yl}-ethyl ester, (4-Cyano -phenyl)-carbamic acid 2-{4-[N'-(3-methyl-benzylidene)-hydrazino]-6-morpholin-4-yl -pyrimidin-2-yl}-ethyl ester, 4-(2-{4-[N'-(3-Methyl-benzylidene)-hydrazino]-6-morpholin-4-yl-pyrimidin-2-yl}-ethoxycarbonylamino)-benzoic acid methyl ester, Phenyl-carbamic acid 2-{4-[N'-(3-methyl-benzylidene)-hydrazino]-6-morpholin-4-yl-pyrimidin-2-yl}-ethyl ester, N-(3-Methyl-benzylidene)-N'-{6-morpholin-4-yl-2-[2-(5-pyridin-4-yl-4H -[1,2,4]triazol-3-ylsulfanyl)-ethyl]-pyrimidin-4-yl}-hydrazine, m-Tolyl-carbamic acid 1,1-dimethyl-3-{4-[N'-(3-methyl-benzylidene)-hydrazino]-6-morpholin-4-yl-pyrimidin-2-yl}-propyl ester, (3-Trifluoromethyl-phenyl)-carbamic acid 1,1-dimethyl-3-{4-[N'-(3-methyl -benzylidene)-hydrazino]-6-morpholin-4-yl-pyrimidin-2-yl}-propyl ester, (3-Trifluoromethyl-phenyl) -carbamic acid 1,1-dimethyl-2-{4-[N'-(3-methyl-benzylidene)-hydrazino]-6-morpholin-4-yl -pyrimidin-2-yl}-ethyl ester, or (4-Trifluoromethyl-phenyl)-carbamic acid 1,1-dimethyl-2-{4-[N'-(3-methyl-benzylidene)-hydrazino]-6-morpholin-4-yl-pyrimidin-2-yl}-ethyl ester.

32. A compound of claim 1, wherein the compound is N-(2-{4-[N'-(3-Methyl-benzylidene)-hydrazino]-6-morpholin-4-yl-pyrimidin-2-yloxy}-ethyl)-N'-phenyl-cyanoguanidine, N-Acetyl-N'-(2-{4-[N'-(3-chloro-benzylidene)-hydrazino]-6-morpholin-4-yl-pyrimidin-2-yloxy}-ethyl)-N"-propyl-guanidine, N'-{4-[N'-(2,2-Dimethyl-benzo[1,3]dioxol-5-ylmethyl)-hydrazino]-6-morpholin-4-yl-pyrimidin-2-ylmethyl}-N,N-dimethyl-guanidine, N-[Dimethylamino-({4-[N'-(2,2-dimethyl-benzo[1,3]dioxol-5-ylmethyl)-hydrazino]-6-morpholin-4-yl-pyrimidin-2-ylmethyl}-amino)-methylene]-methanesulfonamide, N-(Benzylamino-{[4-(6-methyl-benzothiazol-2-ylamino)-6-morpholin-4-yl-pyrimidin-2-ylmethyl]-amino}-methylene)-methanesulfonamide, N -Benzyl-N'-[4-morpholin-4-yl-6-(2-p-tolyl-vinylamino)-pyrimidin-2-ylmethyl]-nitroguanidine, N-[4-(N'-Benzofuran-2-ylmethylene-hydrazino)-6-morpholin-4-yl-pyrimidin-2-ylmethyl]-N'-(4-chloro-benzyl)-N'''-(4-nitro-benzoyl)-guanidine, N-[4-(6-Methyl-benzothiazol-2-ylamino)-6-morpholin-4-yl-pyrimidin-2-ylmethyl]-N'-(4-methyl-benzenesolfonyl)-guanidine, N,N-Dimethyl-N'-(2-{4-[N'-(3-methyl-benzylidene)-hydrazino]-6-morpholin-4-yl-pyrimidin-2-yloxy}-ethyl)-guanidine, 3-{4-[N'-(3-Methyl-benzylidene)-hydrazino]-6-morpholin-4-yl-pyrimidin-2-yl}-propionic acid N'-phenyl-hydrazide, Isobutyric acid N'-(3-{4-[N'-(3-methyl-benzylidene)-hydrazino]-6-morpholin-4-yl-pyrimidin-2-yl}-propionyl)-hydrazide, N-Methyl-N-(2-{4-[N'-(3-methyl-benzylidene)-hydrazino]-6-morpholin-4-yl -pyrimidin-2-yloxy}-ethyl)-O-pyridin-3-yl-hydroxylamine, N-(3,4-Difluoro-benzyl)-N'-(2-{4-morpholin-4-yl-6-[N'-(3-trifluoromethyl-benzylidene)-hydrazino]-pyrimidin-2-yloxy}-ethyl)-guanidine, 1-Isopropyl-3-(3-{4-[N'-(3-methyl-benzylidene)-hydrazino]-6-morpholin-4-yl -pyrimidin-2-yl}-propyl)-sulfamide, 1-Benzyl-3-{4-[N'-(2,2-dimethyl-benzo[1,3]dioxol-5-ylmethylene)-hydrazino]-6-morpholin-4-yl-pyrimidin-2-ylmethyl}-sulfamide, N-(3-Methyl -benzylidene)-N'-(6-morpholin-4-yl-2-{2-[N-(3-trifluoromethyl-phenyl)-hydrazino]-ethoxy}-pyrimidin-4-yl)-hydrazine, N-[({4-[N'-(2,2-Dimethyl-benzo[1,3]dioxol-5-ylmethylene)-hydrazino]-6-morpholin-4-yl-pyrimidin-2-ylmethyl}-amino)-(N'-phenyl-hydrazino)-methylene]-methanesulfonamide, 1-Methanesulfonyl-3-(2-{4-[N'-(4-chloro-benzylidene)-hydrazino]-6-morpholin-4-yl-pyrimidin-2-yloxy}-ethyl)-urea, N-(2-{4-[N'-(4-Chloro-benzylidene)-hydrazino]-6-morpholin-4-yl-pyrimidin-2-yloxy}-ethyl)-cyanoguanidine, N-(2-{4-[N'-(3-Methyl-benzylidene)-hydrazino]-6-morpholin-4-yl -pyrimidin-2-yloxy}-ethyl)-pyrrolidine-1-(N-cyano)carboxamidine, 1-Benzyl-3-(3-{4-[N'-(3-chloro-benzylidene)-hydrazino]-6-morpholin-4-yl-pyrimidin-2-yl}-propyl)-thiourea, [6-[N'-(3-Chloro-benzylidene)-hydrazino]-2-(3-methylamino-propyl)-pyrimidin-4-yl]-dimethyl -amine, 1,1-Dimethyl-3-(2-{4-[N'-(3-methyl-benzylidene)-hydrazino]-6-morpholin-4-yl -pyrimidin-2-yl}-ethyl)-sulfamide, Morpholine-4-carboxylic acid 2-{2-[N'-(3-methyl-benzylidene)-hydrazino]-6-morpholin-4-yl-pyrimidin-4-yloxy}-ethyl ester, Methyl-(3-{2-[N'-(3-methyl-benzylidene)-hydrazino]-6-morpholin-4-yl-pyrimidin-4-yl}-propyl)-silanediol, ({2-[N'-(3-Methyl-benzylidene)-hydrazino]-6-morpholin-4-yl-pyrimidine-4-carbonyl}-amino)-acetic acid, 2-{[4-Morpholin-4-yl-6-(2-oxo-2,3-dihydro-1H-indol-5-ylmethyleneaminooxy)-pyrimidin-2-ylmethyl]-amino}-acetamide, 4-Morpholin-4-yl-6-[N'-(2-oxo-2,3-dihydro-1H-indol-5-ylmethylene)-hydrazino]-pyrimidine-2-carboxylic acid (2-hydroxy-1-methylcarbamoyl-ethyl)-amide, 4-[N'-(3-Methyl-benzylidene)-hydrazino]-6-morpholin-4-yl-pyrimidine-2-carboxylic acid [1-(1-carbamoyl-3-methyl-butylcarbamoyl)-2-hydroxy-ethyl]-amide, 4-Morpholin-4-yl-6-[N'-(2-oxo-2,3-dihydro-1H-indol-5-ylmethylene)-hydrazino]-pyrimidine-2-carboxylic acid (1-carbamoyl-2-phenyl-ethyl)-amide, 2-Amino-3-methyl-N-{4-morpholin-4-yl-6-[N'-(2-oxo-2,3-dihydro-1H-indol-5-ylmethylene)-hydrazino]-pyrimidin-2-ylmethyl}-butyramide, N-(1-Carbamoyl-ethyl)-3-{4-morpholin-4-yl-6-[N'-(2-oxo-2,3-dihydro-1H-indol-5-ylmethylene)-hydrazino]-pyrimidin-2-yl}-propionamide, 4-Morpholin-4-yl-6-[N'-(2-oxo-2,3-dihydro-1H-indol-5-ylmethylene)-hydrazino]-pyrimidine-2- carboxylic acid (2-morpholin-4-yl-2-oxo-ethyl)-amide, 5-{[2-(1H-Benzoimidazol-2-ylmethoxymethyl)-6-morpholin-4-yl -pyrimidin-4-yl]-hydrazonomethyl}-indan-1-one, 1H-Indole-2-carboxylic acid [4-(N'-indan-1-ylidene-hydrazino)-6-morpholin-4-yl-pyrimidin-2-ylmethyl]-amide, N-{4-[N'-(4-Chloro-benzylidene)-hydrazino]-6-morpholin-4-yl-pyrimidin-2-ylmethyl}-N-methyl-pyrrolidine-1-carboxamidine; Dimethyl-carbamic acid 2-{2-[N'-(3-methyl-benzylidene)-hydrazino]-6-morpholin-4-yl-pyrimidin-4-yloxy}-ethyl ester,

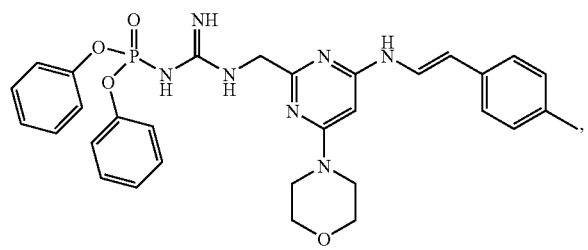

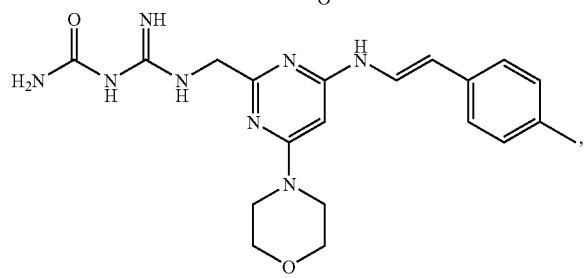

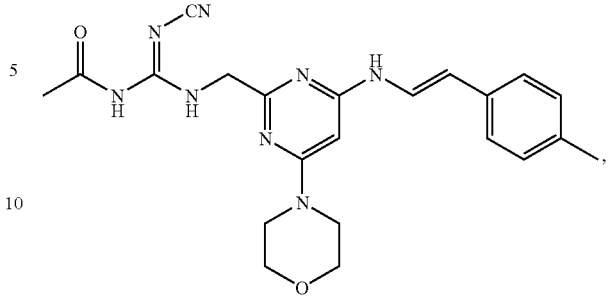

Propyl-carbamic acid 2-{2-[N'-(3-methyl-benzylidene)-hydrazino]-6-morpholin-4-yl -pyrimidin-4-yloxy}-ethyl ester, (4-Methoxy-benzyl)-carbamic acid 2-{2-[N'-(3-methyl-benzylidene)-hydrazino]-6-morpholin-4-yl-pyrimidin-4-yloxy}-ethyl ester, or Pyridin-3-yl -carbamic acid 2-{4-[N'-(3-methyl-benzylidene)-hydrazino]-6-morpholin-4-yl-pyrimidin-2-yloxy}-ethyl ester.

33. A pharmaceutical composition comprising a compound of claim 1, or pharmaceutically acceptable salt thereof, and a pharmaceutically acceptable carrier.

34. A method of treating an IL-12 overproduction-related disorder, selected from rheumatoid arthritis, sepsis, Crohn's disease, multiple sclerosis, psoriasis, and insulin-dependent diabetes mellitus, comprising administering to a subject in need thereof a therapeutically effective amount of a compound of claim 1 or a pharmaceutically acceptable salt thereof.

* * * * *